US012453598B1

(12) United States Patent
Germain et al.

(10) Patent No.: US 12,453,598 B1
(45) Date of Patent: Oct. 28, 2025

(54) ARTHROSCOPIC DEVICES AND METHODS

(71) Applicant: Relign Corporation, Santa Clara, CA (US)

(72) Inventors: Aaron Germain, San Jose, CA (US); Jeff Norton, Emerald Hills, CA (US)

(73) Assignee: Relign Corporation, Santa Clara, CA (US)

( * ) Notice: Subject to any disclaimer, the term of this patent is extended or adjusted under 35 U.S.C. 154(b) by 562 days.

(21) Appl. No.: 17/964,561

(22) Filed: Oct. 12, 2022

Related U.S. Application Data

(63) Continuation of application No. 16/792,099, filed on Feb. 14, 2020, now Pat. No. 11,497,551.

(Continued)

(51) Int. Cl.
*A61B 18/14* (2006.01)
*A61B 17/32* (2006.01)

(Continued)

(52) U.S. Cl.
CPC .................... *A61B 18/1492* (2013.01); *A61B 2017/32004* (2013.01); *A61B 2018/00083* (2013.01);

(Continued)

(58) Field of Classification Search
CPC ...... A61B 18/1492; A61B 2017/32002; A61B 2018/00083; A61B 2018/00565;

(Continued)

(56) References Cited

U.S. PATENT DOCUMENTS 9,855,675 B1 1/2018 Germain et al.
10,022,140 B2 7/2018 Germain et al.

(Continued)

FOREIGN PATENT DOCUMENTS

AU 2020393871 1/2024
CA 3161959 2/2025

(Continued)

OTHER PUBLICATIONS

U.S. Appl. No. 16/792,099, filed Feb. 14, 2020, Arthroscopic Devices and Methods.

(Continued)

*Primary Examiner* — Michael F Peffley
*Assistant Examiner* — Bo Ouyang
(74) *Attorney, Agent, or Firm* — SCHWEGMAN LUNDBERG & WOESSNER, P.A.

(57) ABSTRACT

A tissue resecting device includes an outer sleeve having an axial bore extending along a longitudinal axis from a proximal end to a distal end and opening to an outer window near the distal end. An inner sleeve is rotatably received in the axial bore of the outer sleeve and has an axial channel adapted for communication with a negative pressure source. A distal housing is attached to a distal end of the inner sleeve and has an annular dielectric portion and a circumferentially adjacent annular metal portion having an inner window with circumferentially spaced-apart sharp cutting edges that opens to the axial channel. An active electrode is carried by the annular dielectric portion, and the inner window is circumferentially spaced-part from the active electrode so that the inner window and the active electrode rotate alternately into alignment with the outer window as the inner sleeve is rotated within the outer sleeve.

20 Claims, 26 Drawing Sheets

Related U.S. Application Data

(60) Provisional application No. 62/940,455, filed on Nov. 26, 2019.

(51) Int. Cl.
*A61B 18/00* (2006.01)
*A61B 18/16* (2006.01)

(52) U.S. Cl.
CPC ............... *A61B 2018/00565* (2013.01); *A61B 2018/00577* (2013.01); *A61B 2018/00589* (2013.01); *A61B 2018/00601* (2013.01); *A61B 2018/142* (2013.01); *A61B 2018/162* (2013.01)

(58) Field of Classification Search
CPC ........... A61B 2018/00577; A61B 2018/00589; A61B 2018/00601; A61B 2018/142; A61B 2018/162
See application file for complete search history.

(56) References Cited

U.S. PATENT DOCUMENTS

| | | | |
|---|---|---|---|
| 10,052,149 | B2 | 8/2018 | Germain et al. |
| 10,595,889 | B2 | 3/2020 | Germain et al. |
| 11,497,551 | B2 | 11/2022 | Germain et al. |
| 2008/0188848 | A1 | 8/2008 | Deutmeyer et al. |
| 2013/0274732 | A1 | 10/2013 | Wiener et al. |
| 2013/0331833 | A1 | 12/2013 | Bloom |
| 2015/0173827 | A1 | 6/2015 | Bloom et al. |
| 2015/0265337 | A1 | 9/2015 | Bloom |
| 2015/0327880 | A1 | 11/2015 | Wasicek et al. |
| 2017/0224368 | A1 | 8/2017 | Germain et al. |
| 2017/0252099 | A1 | 9/2017 | Orczy-Timko et al. |
| 2017/0258519 | A1 | 9/2017 | Germain et al. |
| 2019/0328417 | A1 | 10/2019 | Germain |
| 2019/0328448 | A1 | 10/2019 | Germain et al. |
| 2021/0153931 | A1 | 5/2021 | Germain et al. |

FOREIGN PATENT DOCUMENTS

| | | | |
|---|---|---|---|
| EP | 4065011 | | 2/2025 |
| JP | 2023503384 | A | 1/2023 |
| JP | 2024036679 | | 3/2024 |
| WO | WO-2018067248 | A1 | 4/2018 |
| WO | WO-2021108456 | A1 | 6/2021 |

OTHER PUBLICATIONS

"U.S. Appl. No. 16/792,099, Advisory Action mailed Feb. 16, 2021", 2 pgs.
"U.S. Appl. No. 16/792,099, Final Office Action mailed May 13, 2022", 17 pgs.
"U.S. Appl. No. 16/792,099, Final Office Action mailed Dec. 9, 2020", 15 pgs.
"U.S. Appl. No. 16/792,099, Non Final Office Action mailed Jul. 31, 2020", 21 pgs.
"U.S. Appl. No. 16/792,099, Non Final Office Action mailed Oct. 28, 2021", 18 pgs.
"U.S. Appl. No. 16/792,099, Notice of Allowance mailed Jul. 21, 2022", 9 pgs.
"U.S. Appl. No. 16/792,099, Response filed Jan. 27, 2022 to Non Final Office Action mailed Oct. 28, 2021", 10 pgs.
"U.S. Appl. No. 16/792,099, Response filed Feb. 9, 2021 to Final Office Action mailed Dec. 9, 2020", 9 pgs.
"U.S. Appl. No. 16/792,099, Response filed Jun. 24, 2022 to Final Office Action mailed May 13, 2022", 9 pgs.
"International Application Serial No. PCT/US2020/062095, International Preliminary Report on Patentability mailed Jun. 9, 2022", 9 pgs.
"International Application Serial No. PCT/US2020/062095, International Search Report mailed Feb. 11, 2021", 3 pgs.
"International Application Serial No. PCT/US2020/062095, Written Opinion mailed Feb. 11, 2021", 7 pgs.
Allen-Bradley, "AC Braking Basics", Web article, Rockwell Automation, Rockwell International Corporation, [Online]. Retrieved from the Internet: <http://literature.rockwellautomation.com/idc/groups/literature/documents/wp/drives-wp004_-enp.pdf>, (Feb. 2001), 4 pgs.
Allen-Bradley, "What Is Regeneration? Braking / Regeneration Manual: Regeneration (Overview", Revision 1.0. Rockwell Automation, [Online]. Retrieved from the Internet: <https://www.ab.com/supportlabdrives/documentation/techpapers/RegenOverview01.pdf> Accessed Apr. 24, 2017, 6 pgs.
"Australian Application Serial No. 2020393871, First Examination Report mailed Apr. 3, 2023", 3 pgs.
"Australian Application Serial No. 2020393871, Response filed May 30, 2023 to First Examination Report mailed Apr. 3, 2023", 13 pgs.
"Australian Application Serial No. 2020393871, Response filed Aug. 22, 2023 to Subsequent Examiners Report mailed Jun. 22, 2023", 30 pgs.
"Australian Application Serial No. 2020393871, Subsequent Examiners Report mailed Jun. 22, 2023", 3 pgs.
"European Application Serial No. 20892308.6, Response to Communication pursuant to Rules 161(2) and 162 EPC filed Jan. 16, 2023", 14 pgs.
"European Application Serial No. 20892308.6, Extended European Search Report mailed Nov. 6, 2023", 8 pgs.
"Japanese Application Serial No. 2022-556454, Examiners Decision of Final Refusal mailed Oct. 10, 2023", w/ English Translation, 5 pgs.
"Japanese Application Serial No. 2022-556454, Office Action mailed Apr. 18, 2023", w/ English Translation, 7 pgs.
"Japanese Application Serial No. 2022-556454, Response filed Jul. 18, 2023 to Office Action mailed Apr. 18, 2023", w/ English claims, 19 pgs.
"Canadian Application Serial No. 3,161,959, Office Action mailed Aug. 11, 2023", 4 pgs.
"Canadian Application Serial No. 3,161,959, Response filed Nov. 27, 2023 to Office Action mailed Aug. 11, 2023", 16 pgs.
"European Application Serial No. 20892308.6, Response Filed Jan. 19, 2024 to Extended European Search Report mailed Nov. 6, 2023", 40 pgs.

ARTHROSCOPIC DEVICES AND METHODS

CROSS-REFERENCE TO RELATED APPLICATIONS

This application is a continuation of U.S. patent Ser. No. 16/792,099, filed Feb. 14, 2020, which claims the benefit of U.S. Provisional No. 62/940,455, filed Nov. 26, 2019, the entire contents of each of which is incorporated herein by reference.

BACKGROUND OF THE INVENTION

1. Field of the Invention

The present invention relates generally to medical devices and methods, and more particularly to a medical system including a motor-driven tubular cutter configured for both mechanical cutting and electrosurgical cutting, ablation and coagulation procedures.

2. Description of the Background Art

In endoscopic and other surgical procedures including subacromial decompression, anterior cruciate ligament reconstruction involving notchplasty, and arthroscopic resection of the acromioclavicular joint, there is a need for cutting and removal of bone and soft tissue. Currently, surgeons use arthroscopic shavers and burrs having rotational cutting surfaces to remove hard tissue in such procedures.

To promote efficiency, endoscopic tool systems including a reusable handpiece and a selection of interchangeable tool probes having different working ends have been proposed. Such working ends may each have two or more functionalities, such as soft tissue removal and hard tissue resection, so such tools systems can provide dozens of specific functionalities, providing great flexibility.

Of particular interest to the present invention, tool probes can be provided with both mechanical cutting and electrosurgical ablation capabilities. Mechanical cutters are often the most efficient choice for cutting and resecting hard tissues, such as bone, while electrosurgical ablation is often preferred for treating soft tissues. However, the ablation electrodes on such tools can also be used to deliver an electrical current to cauterize bleeding tissue resulting from ablation, cutting, or other trauma during a procedure.

One problem, however, with such combined mechanical/electrosurgical ablation probes is that the delivery of an ablation current from the ablation electrode can degrade the mechanical cutting blade. Such degradation is a particular problem with sharp metal cutting edges where the inventors herein have found that the ablation current can focus on the sharp metal cutting edges, quickly rendering them unsuitable for cutting hard tissues.

It is therefore an object of the present invention to provide improved surgical systems and methods for their use, such as improved arthroscopic tissue cutting and removal system wherein a motor-driven electrosurgical device is provided for cutting and removing bone or soft tissue from a joint or other site. It is a further object of the present invention to provide combined mechanical/electrosurgical cutters where degradation of the mechanical cutting element is reduced or eliminated. In particular, it would be desirable to provide metal cutters having cutting windows with sharp cutting edges which can be exposed to both ablation and cauterizing currents without loss to ability to mechanically cut hard tissues, such as bone. At least some of these objectives will be met by the inventions described herein

SUMMARY OF THE INVENTION

The present invention provides a combination mechanical resection and electrosurgical treatment probe suitable for arthroscopic and other endoscopic and minimally invasive medical procedures. In particular, the probe of the present invention includes a rotating inner sleeve member with a distal inner window having sharp metal cutting edges that is rotatable in an outer sleeve having a distal outer window with cooperating sharp metal edges. The rotating inner sleeve member will typically have a tubular configuration and have a vacuum-assisted extraction channel therethrough. An active electrosurgical electrode is carried on the rotating inner sleeve, typically located at or near a location at or near the distal end which opposes the inner window. In a method of use, rotation of the inner sleeve member can be stopped to position and expose the active electrosurgical electrode in the outer window of the outer sleeve. The active surgical electrode is used to selectively deliver ablation current as well as cauterizing current. Delivery of an ablation current when the active surgical electrode is in proximity to the sharp metal edges of the outer window has been found by the inventors herein to present a substantial risk of degrading the sharp outer window edges due to a concentrated current flux at such sharp edges. The inventors herein, however, have further found that the sharp metal edges of the outer window can be protected and preserved by locating a return electrode surface on the rotating inner sleeve member where the return electrode surface is positioned between the ablation electrode and sharp edges of the outer window when the active surgical electrode is positioned (typically rotationally center) within the outer cutting window. In particular, by locating the return electrode surface on the inner sleeve member so that it is closer to the ablation electrode than to an outer window edge (while maintaining a sufficient distance to allow bipolar current flow in the treatment environment), the return current can be preferentially directed to the inner sleeve's return electrode surface with less current being received by the metal edges of the outer window which form a return electrode surface. In this way, the inventors herein believe that current concentrations at the sharp edges of the outer window may be sufficiently reduced to lessen or eliminate degradation of such sharp edges. Such sharpened outer window edges are at high risk of degradation at least in part due to current concentration that is found on all sharp metal edges. By directing the return current to a return electrode surface which is generally free from such current-concentrating features, and away from the outer window edges, the sharpness of the outer window edges can be preserved.

In the first aspect of the present invention, a tissue resecting device comprises an outer sleeve and an inner sleeve. The outer sleeve has an axial bore extending along a longitudinal axis from a proximal end to a distal end and opening to an outer window near the distal end. The inner sleeve member is rotatably received in the axial bore of the outer sleeve and has an axial channel adapted for communication with a negative pressure source. A distal housing is attached to a distal end of the inner sleeve, and the distal housing comprises an annular dielectric portion and a circumferentially adjacent annular metal portion having an inner window with circumferentially spaced-part sharp cutting edges that open to the axial channel. An active electrode is carried on the annular dielectric portion, and the inner window is circumferentially spaced apart from the active electrode such that the inner window and the active electrode rotate alternatively into alignment with the outer window as the outer as the inner sleeve member is rotated within the outer sleeve.

In particular embodiments, the outer window in the outer sleeve is circumferentially wider than the annular dielectric portion of the distal housing so that the annular dielectric portion may be stopped within the outer window leaving marginal portions of the annular metal portion exposed between the annular dielectric portion and at least one edge of the outer window so that the exposed annular metal portion acts as a return electrode preventing current concentration at the at least one edge of the outer window. That is, the return electrode defined by the annular metal portion of the distal housing will preferentially collect current from the active electrode since the return electrode is closer to and larger than the edge of the outer window, thus limiting or eliminating damage to the edge of the outer window that might otherwise occur if the edge acted as a primary return electrode In further embodiments, the annular metal portion and the annular dielectric portion will extend a full 360° about a transverse cross-section of the distal housing portion that is proximal to the inner window. In specific instances, the electrode will be mounted on the annular dielectric portion (typically in a channel or recess so that an outer surface of the active electrode will follow the same outer curvature as the annular dielectric portion) and have a surface that extends over an arc in a range of at least about 20° of the transverse cross-section, while the annular dielectric portion has surfaces extending over an arc on each side of the electrode in a range of at least 10° of the transverse cross-section, and the annular metal portion has side walls on each side of the inner window extending over an arc in a range of at least 10° of the transverse cross-section.

In further instances, a distance between each sharp cutting edge of the annular metal portion and the adjacent annular dielectric portion extends over an arc of at least 10°. Such a distance assures that the active electrode and the adjacent return electrode are separated by minimum distance to allow optimal bipolar operation. Typically, the surface of the active electrode will span a circumferential distance of at least 0.03 inches, and the active electrode edges are spaced-apart from the closest surface of the annular metal portion (which forms return electrode) at least 0.01 inches.

In other exemplary embodiments, the cross-section of the distal housing and the region of the active electrode, dielectric surface and return electrode, will have a generally circular cross-section, with the active electrode having a radius R1, the outer surface of the annular dielectric portion having a radius R2, and the outer surface of the annular metal portion having a radius R3. Typically, R1 would be less than R2 by a distance of 0.02 inches or less and R2 may be less than R3 by a distance of 0.02 inches or less. Such small differences allow the electrode and the annular dielectric portion to be slightly inset relative to the cylindrical surface of the annular metal portion, reducing the risk of wear and degradation to the active electrode during rotation.

In particular embodiments of the tissue resecting device of the present invention, the active electrode has an outer surface that is diametrically opposed to the inner window formed in the annular metal portion of the distal housing. The dielectric portion is also diametrically opposed to the inner window. During use of the device, a controller is configured to stop rotation of the inner sleeve to position and expose the electrode and dielectric portion in the outer window of the outer sleeve. By providing a selected circumferential spacing between the active electrode and the sharp edges of the outer window, and positioning the return electrode portion of the inner sleeve in that space, degradation of the sharp edges of the outer window is minimized. In particular, locating the surface area of the return electrode formed by the annular metal portion between the active electrode and the sharp metal edges of the outer window reduces the current concentration experienced by the outer window edges. The present invention is not limited to the active electrode and dielectric portion being diametrically opposed to the inner window, and the electrode and dielectric portion may be asymmetrically located relative to the inner window in other embodiments so long as, when the inner sleeve is in a stopped position, a sufficient available return electrode area of the inner sleeve is maintained between the active electrode and the outer window's sharp edges.

In other specific embodiments of the tissue resecting devices of the present invention, the sharp cutting edges on the inner window may be in the form of linear edges, serrated edges, edges having cutting teeth formed therein, and any other form of cutting edge known to be effective with tissues of all types, particularly with hard tissues, such as bone.

In still other specific aspects of the tissue resecting device of the present invention, the distal housing may comprise an electrically conductive tubular structure having an axial channel formed in a wall thereof. A dielectric insert may be disposed in the axial channel to form the annular dielectric portion where the annular metal portion of the distal housing is provided by the adjacent wall of the electrically conductive tubular structure.

In still another aspect of the present invention, a method of resecting tissue comprises providing a probe with an elongated shaft having co-axial outer and inner sleeves with outer and inner resecting windows in their respective distal ends. The inner sleeve member is rotatable in the outer sleeve, and the inner sleeve member carries active and return electrodes. The inner and outer resecting windows are engaged against tissue while rotating or rotationally oscillating the inner sleeve member to thereby resect tissue, and RF current is delivered to the active electrode the electrode to apply energy to tissue. An ablation RF current can be delivered with the inner sleeve in its stopped position to ablate tissue in a first mode. A coagulation RF current can be delivered with the inner sleeve in its stopped position to coagulate bleeding tissue in a second mode. Also, a coagulation RF current can be delivered with the inner sleeve rotating to contemporaneously resect and coagulate tissue in a third mode.

In such instances, an elongate electrical conductor may be disposed in the axial bore of the inner sleeve and can be connected in a distal end to the active electrode and have a proximal end which can be connected to an electrosurgical power source, typically in a hub as described in more detail below.

In further instances, a proximal hub may be attached to the tissue resecting device, typically being fixedly attached to a proximal end of the outer sleeve and rotatably attached to a proximal end of the inner sleeve. The proximal bub will typically be removably connectable to a handle or other handheld unit having a motor configured to rotate the inner sleeve member relative to the outer sleeve and the proximal hub.

The present invention also provides tissue resecting systems comprising any tissue resecting devices as described previously in combination with a handle other handheld unit particularly those tissue resecting devices having a proximal hub configured to rotate the inner sleeve member relative to the outer sleeve and to provide electrical connections to the active electrode and return electrodes. Such tissue resecting systems may further comprise a handpiece configured to removably connect to the proximal hub. The handpiece will typically include a motor drive adapted to rotate the inner sleeve member and an inner window relative to an outer window in the outer sleeve through window-open and window-closed positions. A controller may also be provided in the handle or other handheld unit, where the controller is adapted to selectively drive the motor to rotate the inner sleeve, to stop the motor-driven rotation of the inner sleeve, to deliver ablation current to the active electrode, and to deliver cauterizing current to the active electrode, either individually or in various combinations.

Using such a tissue resecting system, methods of the present invention comprise engaging the outer window of the outer sleeve against a target tissue site and operating the controller to rotate the inner sleeve member and the inner window relative to the outer window to mechanically resect tissue with the sharp cutting edges. While any tissue may be resected, the sharp cutting edges are particularly effective for resecting soft tissue and bone.

The methods further comprise operating the controller to stop rotation of the inner sleeve member with the active electrode aligned in the outer window of the outer sleeve and to deliver an ablation current to the active electrode to ablate tissue. While any type of tissue may be ablated, a radiofrequency and related forms of electrosurgical ablation are particularly effective with soft tissue.

By having mechanical tissue resection available for treating hard tissues such as bone as well as electrosurgical tissue ablation available for treating soft tissue, the same device can be conveniently used to treat both bone and soft tissues in procedures where it is difficult or undesirable to exchange instruments, such as arthroscopic procedures where it may be difficult to reposition a second probe or tool after an initial procedure has been completed with a first probe or tool.

In yet a further aspect, the tissue resecting probe of the present invention will have seals on proximal and distal sides of electrical contact(s) in hub. For example, the proximal hub may be coupled to an elongated outer sleeve extending about a longitudinal axis where a housing of the hub has a distal end with an opening therein. A rotatable inner sleeve member may be configured to rotate in the hub and outer sleeve, where the inner sleeve member extends to a working end passing through the opening. The inner sleeve member may carry an electrical contact ring adapted to rotatably contact a non-rotating electrical contact in an interior of the hub, and first and second annular seals may be carried by the hub which contact and seal the inner sleeve member on proximal and distal sides of the contact ring to provide a fluid-tight seal around the contact ring and non-rotating contact.

In specific instances, the contact ring may be coupled by an electrical lead to an active electrode carried in said working end of the inner sleeve, and the electrical lead may be carried in a passageway inward of a wall of the inner sleeve. The electrical lead may be positioned on an outer wall or within the axial bore of the inner sleeve member to complete a current path. The hub may be configured for detachable coupling with a receiving channel in a handpiece carrying a motor drive, and the receiving channel may carry an active contact adapted for electrically coupling with the non-rotating contact of the hub when the probe is attached to the handpiece. The receiving channel may also carry a return contact that engages an electrical contact in the hub that provides for RF current to a return electrode carried by the outer sleeve.

In a still further aspect, the distal housing of the present invention has a continuous (usually circular) wall having a thickness in a radial direction. A first portion of the wall, typically an annular segment, has a full wall thickness which entirely metal, and a second portion of the wall, typically an annular segment, has a full wall thickness which is entirely ceramic in the radial direction, i.e., the wall structure is not layered which would increase wall thickness and reduce the cross-sectional area available for the axial bore needed to accommodate tissue debris extraction.

For example, the tissue resecting probe may comprise an elongated outer sleeve extending about a longitudinal axis with a distal portion having an outer window that opens to an axial bore therein. An inner sleeve member may be configured to rotate in the bore, and the inner sleeve member may include a distal housing assembly having an inner window that opens to an interior channel. The housing assembly may include a metal wall portion and a ceramic or other dielectric wall portion defining said interior channel, where the full wall thickness along any radial vector is either metal or dielectric, typically a ceramic. Typically, an inner surface of the dielectric wall portion will comprise a surface of the interior channel. An outer surface of the dielectric wall portion may carry an electrode, and the metal wall portion may define lateral cutting edges of the inner window.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to bone cutting and tissue removal devices and related methods of use. Several variations of the invention will now be described to provide an overall understanding of the principles of the form, function and methods of use of the devices disclosed herein. In general, the present disclosure provides for variations of arthroscopic tools adapted for cutting bone, soft tissue, meniscal tissue, and for RF ablation and coagulation. The arthroscopic tools are typically disposable and are configured for detachable coupling to a non-disposable handpiece that carries a motor drive component. This description of the general principles of this invention is not meant to limit the inventive concepts in the appended claims.

Figure 1:
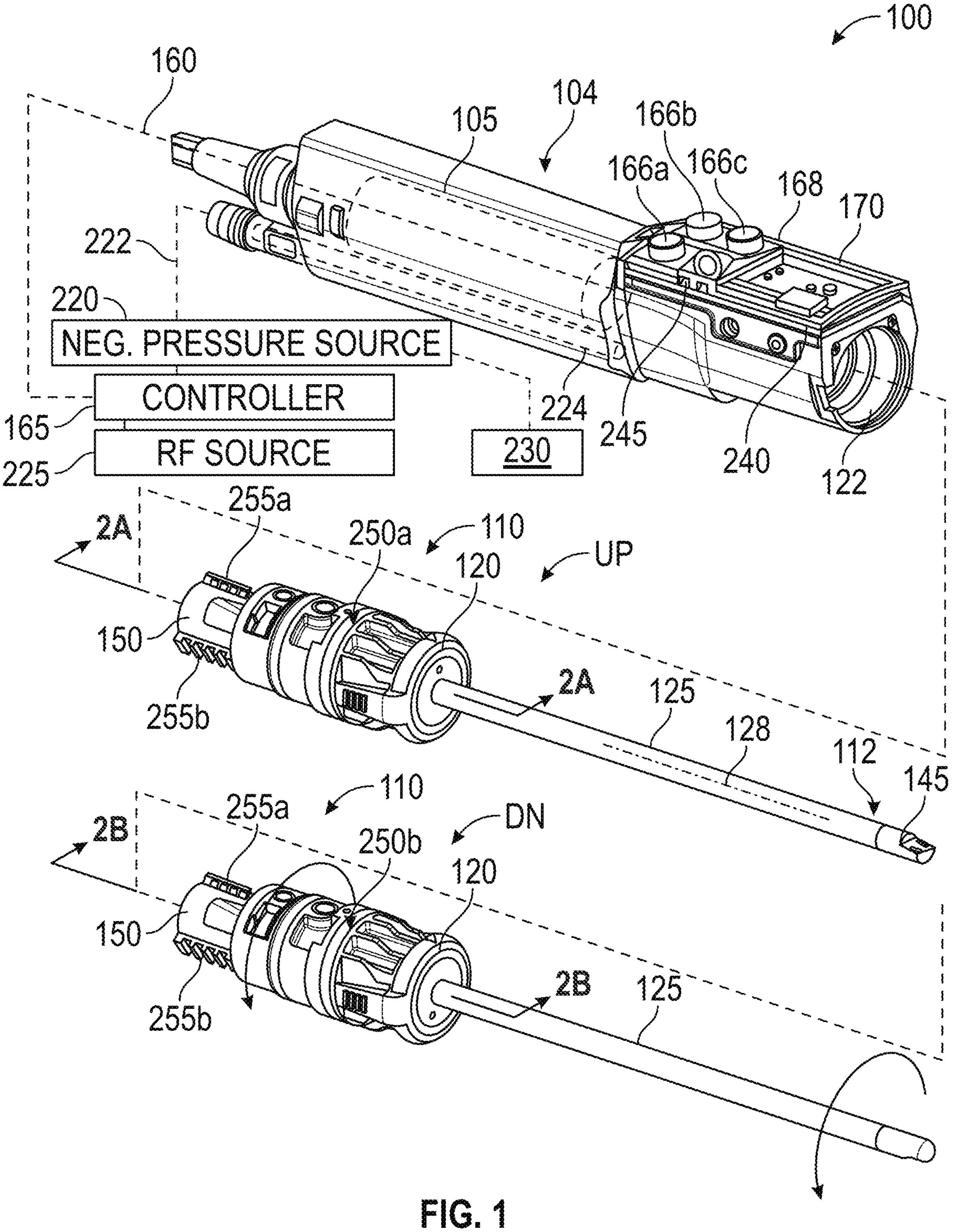
FIG. 1 is a perspective view of an arthroscopic cutting system that includes reusable handpiece with a motor drive and a detachable single-use cutting probe, wherein the cutting probe is shown in two orientations as it may be coupled to the handpiece with the probe and working end in upward orientation or a downward orientation relative to the handpiece, and wherein the handpiece includes an LCD screen for displaying operating parameters of system during use together with control actuators on the handpiece.

In one variation shown in FIG. 1, the arthroscopic system 100 of the present invention provides a handpiece 104 with motor drive 105 and a disposable shaver assembly or probe 110 with a proximal hub 120 that can be received by receiver or bore 122 in the handpiece 104. In one aspect, the probe 110 has a working end 112 that carries a high-speed rotating cutter that is configured for use in many arthroscopic surgical applications, including but not limited to treating bone in shoulders, knees, hips, wrists, ankles and the spine.

Figure 2A:
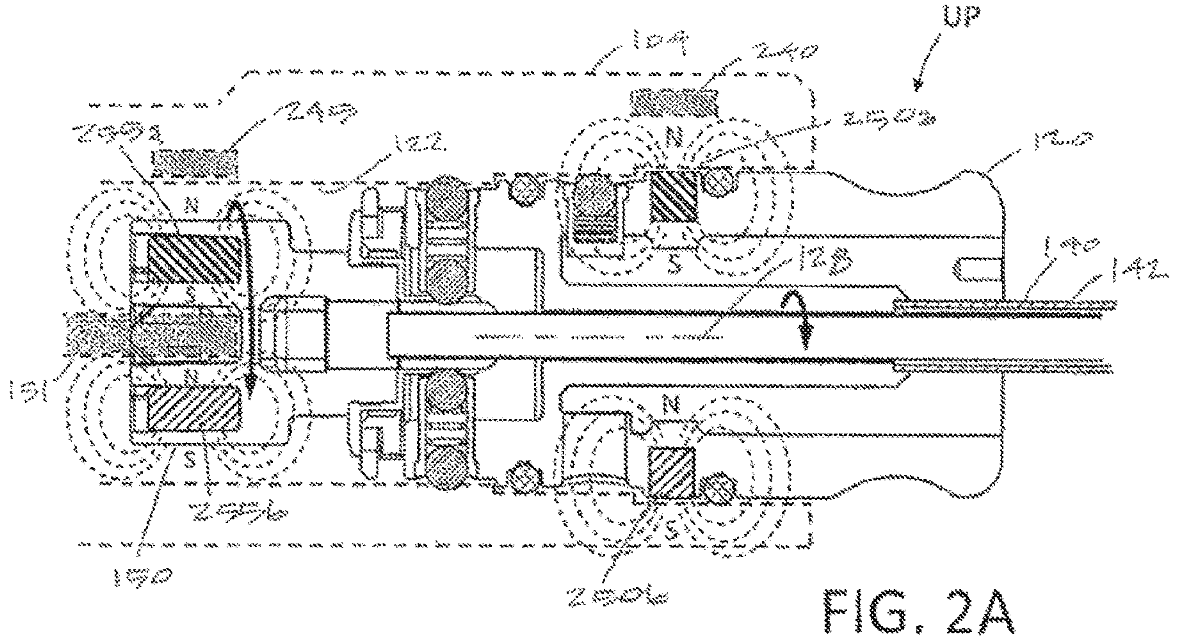
FIG. 2A is an enlarged longitudinal sectional view of the hub of the probe of FIG. 1 taken along line 2A-2A of FIG. 1 with the hub and probe in an upward orientation relative to the handpiece, further showing Hall effect sensors carried by the handpiece and a plurality of magnets carried by the probe hub for device identification, for probe orientation and determining the position of motor driven components of the probe relative to the handpiece.
Figure 3A:
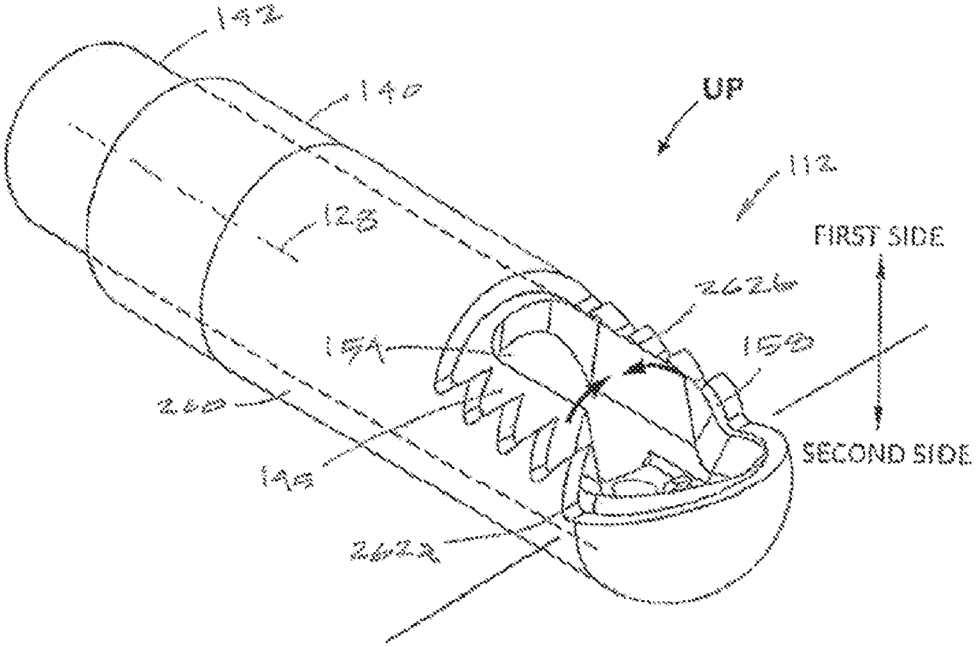
FIG. 3A is an enlarged perspective view of the working end of the probe of FIG. 1 in an upward orientation with the rotatable cutting member in a first position relative to the outer sleeve wherein the window in the cutting member is aligned with the window of the outer sleeve.
Figure 3B:
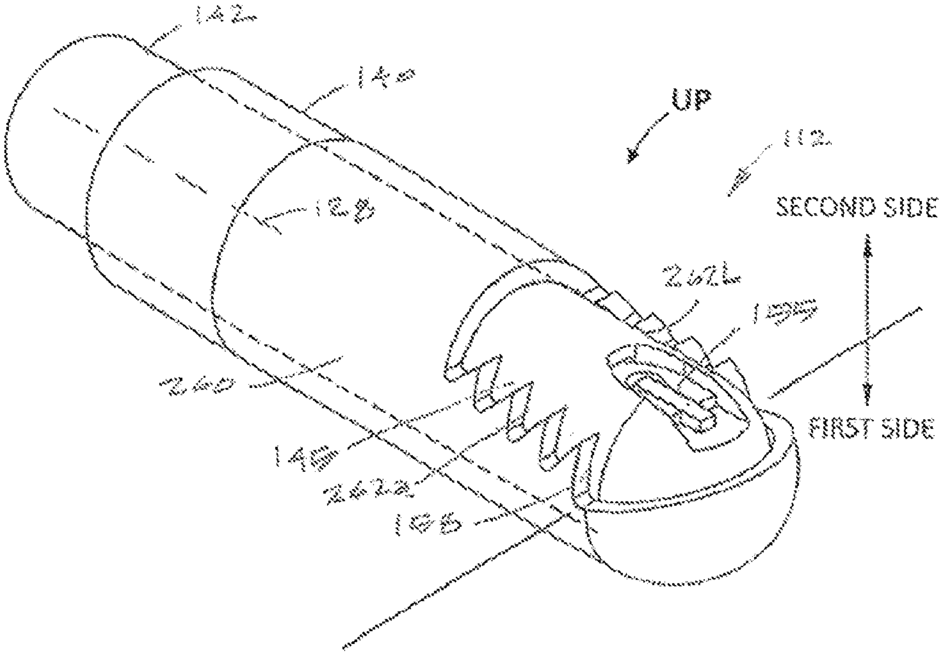
FIG. 3B is a perspective view of the working end of FIG. 1 in an upward orientation with the rotatable cutting member in a second position relative to the outer sleeve wherein the electrode carried by the cutting member is aligned with a centerline of the window of the outer sleeve.

In FIGS. 1, 2A and 3A, it can be seen that probe 110 has a shaft 125 extending along longitudinal axis 128 that comprises an outer sleeve 140 and an inner sleeve member 142 rotatably disposed therein with the inner sleeve member 142 carrying a distal ceramic cutting member 145 (FIG. 3A). The shaft 125 extends from the proximal hub 120 wherein the outer sleeve 140 is coupled in a fixed manner to the hub 120 which can be an injection molded plastic, for example, with the outer sleeve 140 insert molded therein. The inner sleeve member 142 is coupled drive coupling 150 that is configured for coupling to the rotating motor shaft 151 of motor drive unit 105. More in particular, the rotatable cutting member 145 that is fabricated of a ceramic material with sharp cutting edges on opposing sides 152*a* and 152*b* of window 154 therein for cutting soft tissue. The motor drive 105 is operatively coupled to the ceramic cutter to rotate the cutting member at speeds ranging from 1,000 rpm to 20,000 rpm. In FIG. 3B, it can be seen that cutting member 145 also carries an RF electrode 155 in a surface opposing the window 154. The cutting member 145 rotates and shears tissue in the toothed opening or window 158 in the outer sleeve 140 (FIG. 3A). A probe of the type shown in FIG. 1 is described in more detail in co-pending and commonly owned patent application Ser. No. 15/421,264 filed Jan. 31, 2017 titled ARTHROSCOPIC DEVICES AND METHODS which is incorporated herein in its entirety by this reference.

As can be seen in FIG. 1, the probe 110 is shown in two orientations for detachable coupling to the handpiece 104. More particularly, the hub 120 can be coupled to the handpiece 104 in an upward orientation indicated at UP and a downward orientation indicated at DN where the orientations are 180° opposed from one another. It can be understood that the upward and downward orientations are necessary to orient the working end 112 either upward or downward relative to the handpiece 104 to allow the physician to interface the cutting member 145 with targeted tissue in all directions without having to manipulate the handpiece in 360° to access tissue.

In FIG. 1, it can be seen that the handle 104 is operatively coupled by electrical cable 160 to a controller 165 which controls the motor drive unit 105. Actuator buttons 166*a*, 166*b* or 166*c* on the handle 104 can be used to select operating modes, such as various rotational modes for the ceramic cutting member 145. In one variation, a joystick 168 can be moved forward and backward to adjust the rotational speed of the ceramic cutting member 145. The rotational speed of the cutter can continuously adjustable or can be adjusted in increments up to 20,000 rpm. An LCD screen 170 is provided in the handpiece for displaying operating parameters, such as cutting member RPM, mode of operation, etc.

Figure 4:
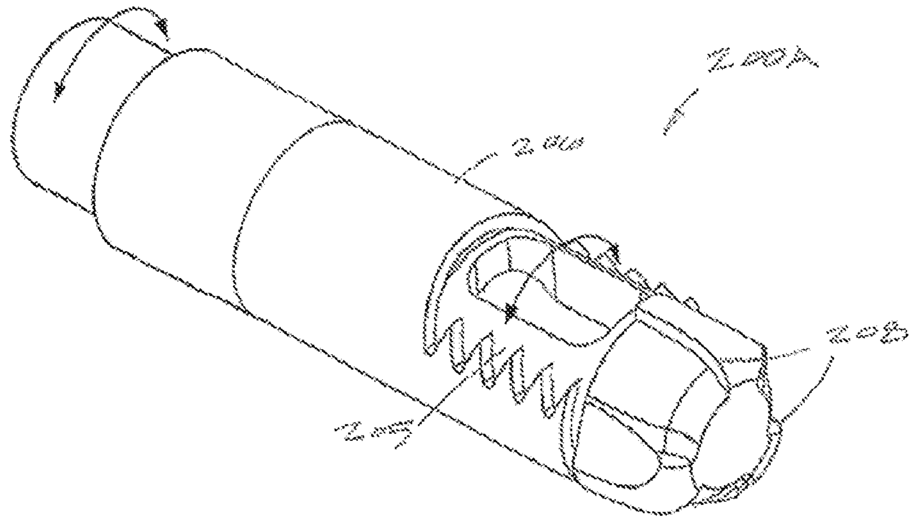
FIG. 4 is a perspective view of a working end of a variation of a probe that may be detachably coupled to the handpiece of FIG. 1, wherein the working end includes a bone burr extending distally from the outer sleeve.
Figure 5:
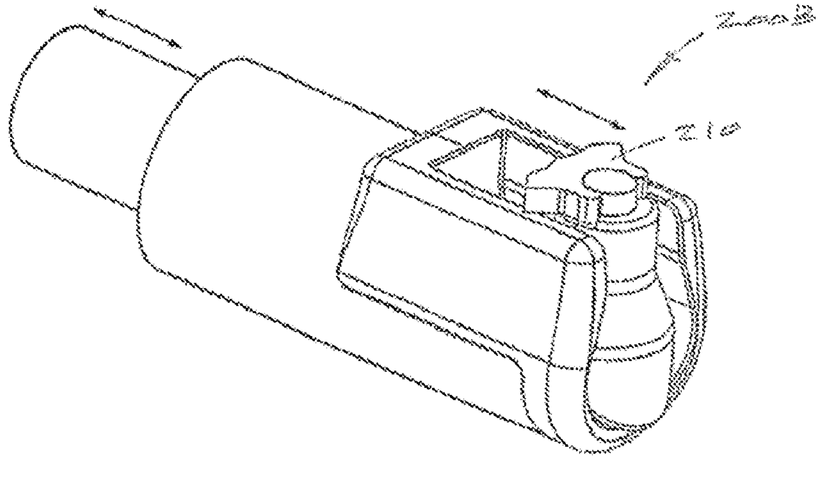
FIG. 5 is a perspective view of a working end of a variation of a probe that may be detachably coupled to the handpiece of FIG. 1, wherein the working end has a reciprocating electrode.
Figure 6:
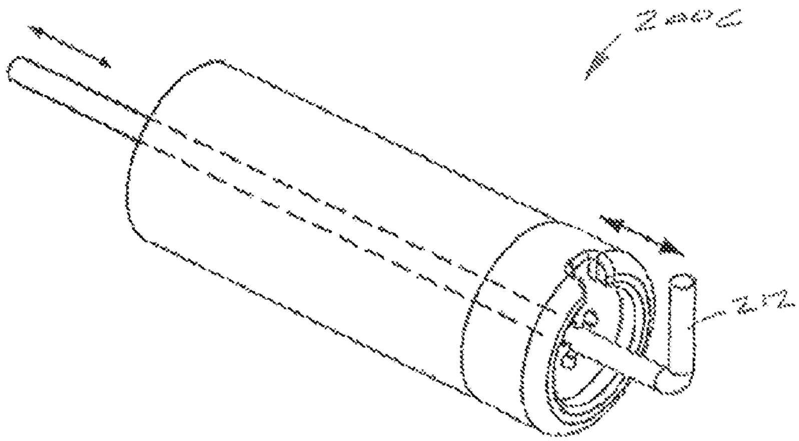
FIG. 6 is a perspective view of a working end of another variation of a probe that may be detachably coupled to the handpiece of FIG. 1, wherein the working end has a hook electrode that has extended and non-extended positions.
Figure 7:
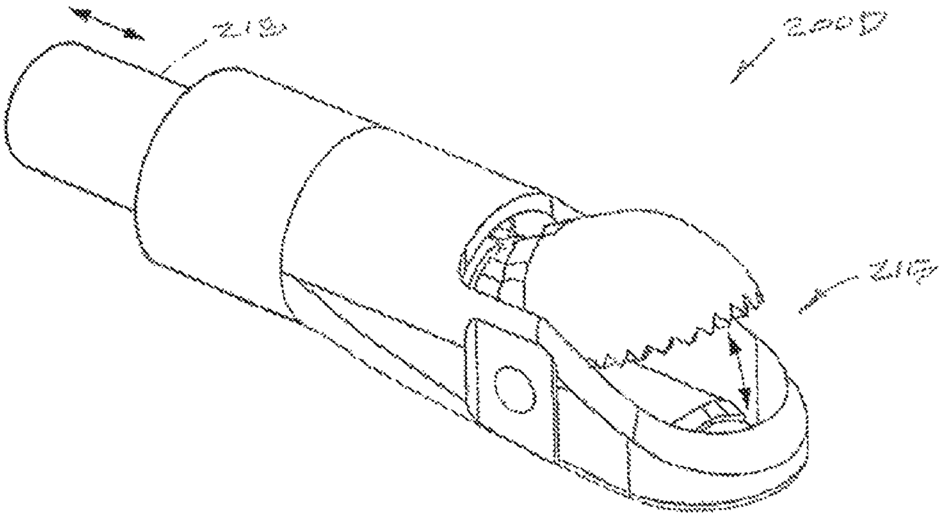
FIG. 7 is a perspective view of a working end of yet another variation of a probe that may be detachably coupled to the handpiece of FIG. 1, wherein the working end has an openable-closeable jaw structure for cutting tissue.

It can be understood from FIG. 1 that the system 100 and handpiece 104 is adapted for use with various disposable probes which can be designed for various different functions and procedures. For example, FIG. 4 illustrates a different variation of a probe working end 200A that is similar to working end 112 of probe 110 of FIGS. 3A-3B, except the ceramic cutting member 205 extends distally from the outer sleeve 206 and the cutting member has burr edges 208 for cutting bone. The probe of FIG. 4 is described in more detail in co-pending and commonly owned patent application Ser. No. 15/271,184 filed Sep. 20, 2016 titled ARTHROSCOPIC DEVICES AND METHODS. FIG. 5 illustrates a different variation of a probe working end 200B with a reciprocating electrode 210 in a type of probe described in more detail in co-pending and commonly owned patent application Ser. No. 15/410,723 filed Jan. 19, 2017 titled ARTHROSCOPIC DEVICES AND METHODS. In another example, FIG. 6 illustrates another variation of a probe working end 200C that has an extendable-retractable hook electrode 212 in a probe type described in more detail in co-pending and commonly owned patent application Ser. No. 15/454,342 filed Mar. 9, 2017 titled ARTHROSCOPIC DEVICES AND METHODS. In yet another example, FIG. 7 illustrates a variation of a working end 200D in a probe type having an openable-closable jaw structure 215 actuated by reciprocating member 218 for trimming meniscal tissue or other tissue as described in more detail in co-pending and commonly owned patent application Ser. No. 15/483,940 filed Apr. 10, 2017 titled ARTHROSCOPIC DEVICES AND METHODS. All of the probes of FIGS. 4-7 can have a hub similar to hub 120 of probe 110 of FIG. 1 for coupling to the same handpiece 104 of FIG. 1, with some of the probes (see FIGS. 5-7) having a hub mechanism for converting rotational motion to linear motion. All of the patent applications just identified in this paragraph are incorporated herein by this reference.

FIG. 1 further shows that the system 100 also includes a negative pressure source 220 coupled to aspiration tubing 222 which communicates with a flow channel 224 in handpiece 104 and can cooperate with any of the probes 110, 200A, 200B or 200C of FIGS. 1-3B, 4, 5 and 6. In FIG. 1 it also can be seen that the system 100 includes an RF source 225 which can be connected to an electrode arrangement in any of the probes 110, 200A, 200B or 200C of FIGS. 1-3B, 4, 5 and 6. The controller 165 and microprocessor therein together with control algorithms are provided to operate and control all functionality, which includes controlling the motor drive 105 to move a motor-driven component of any probe working end 110, 200A, 200B or 200C, as well as for controlling the RF source 225 and the negative pressure source 220 which can aspirate fluid and tissue debris to collection reservoir 230.

As can be understood from the above description of the system 100 and handpiece 104, the controller 165 and controller algorithms need to be configured to perform and automate many tasks to provide for system functionality. In a first aspect, controller algorithms are needed for device identification so that when any of the different probes types 110, 200A, 200B, 200C or 200D of FIGS. 1 and 4-7 are coupled to handpiece 104, the controller 165 will recognize the probe type and then select algorithms for operating the motor drive 105, RF source 225 and negative pressure source 220 as is needed for the particular probe. In a second aspect, the controller is configured with algorithms that identify whether the probe is coupled to the handpiece 104 in an upward or downward orientation relative to the handpiece, wherein each orientation requires a different subset of the operating algorithms. In another aspect, the controller has separate control algorithms for each probe type wherein some probes have a rotatable cutter while others have a reciprocating electrode or jaw structure. In another aspect, most if not all the probes 110, 200A, 200B, 200C and 200D (FIGS. 1, 4-7) require a default "stop" position in which the motor-driven component is stopped in a particular orientation within the working end. For example, a rotatable cutter 145 with an electrode 155 needs to have the electrode centered within an outer sleeve window 158 in a default position such as depicted in FIG. 3B. Some of these systems, algorithms and methods of use are described next.

Figure 2B:
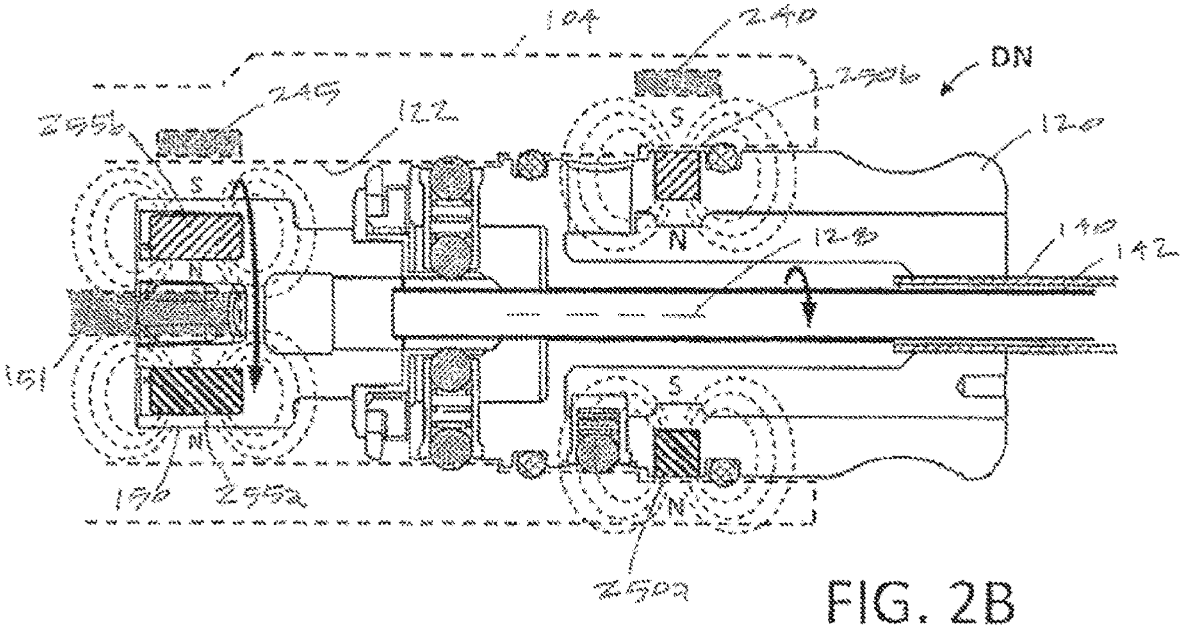
FIG. 2B is a sectional view of the hub of FIG. 1 taken along line 2B-2B of FIG. 1 with the hub and probe in a downward orientation relative to the handpiece showing the Hall effect sensor and magnets having a different orientation compared to that of FIG. 2A.

Referring to FIGS. 1 and 2A-2B, it can be seen that handpiece 104 carries a first Hall effect sensor 240 in a distal region of the handpiece 104 adjacent the receiving passageway 122 that receives the hub 120 of probe 110. FIG. 2A corresponds to the probe 110 and working end 112 in FIG. 1 being in the upward orientation indicated at UP. FIG. 2B corresponds to probe 110 and working end 112 in FIG. 1 being in the downward orientation indicated at DN. The handpiece 104 carries a second Hall effect sensor 245 adjacent the rotatable drive coupling 150 of the probe 110. The probe 110 carries a plurality of magnets as will be described below that interact with the Hall effect sensors 240, 245 to provide multiple control functions in cooperation with controller algorithms, including (i) identification of the type of probe coupled to the handpiece, (ii) the upward or downward orientation of the probe hub 120 relative to the handpiece 104, and (iii) the rotational position and speed of rotating drive collar 150 from which a position of either rotating or reciprocating motor-driven components can be determined.

The sectional views of FIGS. 2A-2B show that hub 120 of probe 110 carries first and second magnets 250*a* and 250*b* in a surface portion thereof. The Hall sensor 240 in handpiece 104 is in axial alignment with either magnet 250*a* or 250*b* when the probe hub 120 is coupled to handpiece 104 in an upward orientation (FIGS. 1 and 2A) or a downward orientation (FIGS. 1 and 2B). In one aspect as outlined above, the combination of the magnets 250*a* and 250*b* and the Hall sensor 240 can be used to identify the probe type. For example, a product portfolio may have from 2 to 10 or more types of probes, such as depicted in FIGS. 1 and 4-7, and each such probe type can carry magnets 250*a*, 250*b* having a specific, different magnetic field strength. Then, the Hall sensor 240 and controller algorithms can be adapted to read the magnetic field strength of the particular magnet(s) in the probe which can be compared to a library of field strengths that correspond to particular probe types. Then, a Hall identification signal can be generated or otherwise provided to the controller 165 to select the controller algorithms for operating the identified probe, which can include parameters for operating the motor drive 105, negative pressure source 220 and/or RF source 225 as may be required for the probe type. As can be seen in FIGS. 1, 2A and 2B, the probe hub 120 can be coupled to handpiece 104 in upward and downward orientations, in which the North (N) and South(S) poles of the magnets 250*a*, 250*b* are reversed relative to the probe axis 128. Therefore, the Hall sensor 240 and associated algorithms look for magnetic field strength regardless of polarity to identify the probe type.

Referring now to FIGS. 1, 2A-2B and 3A-3B, the first and second magnets 250*a* and 250*b* with their different orientations of North (N) and South(S) poles relative to central longitudinal axis 128 of hub 120 are also used to identify the upward orientation UP or the downward orientation DN of hub 120 and working end 112. In use, as described above, the physician may couple the probe 110 to the handpiece receiving passageway 122 with the working end 112 facing upward or downward based on his or her preference and the targeted tissue. It can be understood that controller algorithms adapted to stop rotation of the cutting member 145 in the window 158 of the outer sleeve 104 of working end 112 need to "learn" whether the working end is facing upward or downward, because the orientation or the rotating cutting member 145 relative to the handpiece and Hall sensor 240 would vary by 180°. The Hall sensor 240 together with a controller algorithm can determine the orientation UP or the downward orientation DN by sensing whether the North (N) or South(S) pole of either magnet 250*a* or 250*b* is facing upwardly and is proximate the Hall sensor 240.

In another aspect of the invention, in probe 110 (FIG. 1) and other probes, the motor-driven component of a working end, such as rotating cutter 145 of working end 112 of FIGS. 1 and 3A-3B, needs to be stopped in a selected rotational position relative to a cut-out opening or window 158 in the outer sleeve 140. Other probe types may have a reciprocating member, or a jaw structure as described above, which also needs a controller algorithm to stop movement of a moving component in a selected position, such as the axial-moving electrodes of FIGS. 5-6 and the jaw structure of FIG. 7. In all probes, the motor drive 105 couples to the rotating drive coupling 150, thus sensing the rotational position of the drive coupling 150 can be used to determine the orientation of the motor-driven component in the working end. More in particular, referring to FIGS. 1 and 2A-2B, the drive coupling 150 carries third and fourth magnets 255*a* or 255*b* with the North (N) and South(S) poles of magnets 255*a* or 255*b* being reversed relative to the probe axis 128. Thus, Hall sensor 245 can sense when each magnet rotates passes the Hall sensor and thereby determine the exact rotational position of the drive coupling 150 twice on each rotation thereof (once for each magnet 255*a*, 255*b*). Thereafter, a controller tachometer algorithm using a clock can determine and optionally display the RPM of the drive coupling 150 and, for example, the cutting member 145 of FIG. 3A.

In another aspect of the invention, the Hall sensor 245 and magnets 255*a* and 255*b* (FIGS. 1 and 2A) are used in a set of controller algorithms to stop the rotation of a motor-driven component of a working end, for example, cutting member 145 of FIGS. 1 and 3A-3B in a pre-selected rotational position. In FIG. 3A, it can be seen that the inner sleeve member 142 and a "first side" of cutting member 145 and window 154 therein is stopped and positioned in the center of window 158 of outer sleeve 140. The stationary position of cutting member 145 and window 154 in FIG. 3A may be used for irrigation or flushing of a working space to allow for maximum fluid outflow through the probe.

FIG. 3B depicts inner sleeve member 142 and a "second side" of cutting member 145 positioned about the centerline of window 158 in the outer sleeve 140. The stationary or stopped position of cutting member 145 in FIG. 3B is needed for using the RF electrode 155 to ablate or coagulate tissue. It is important that the electrode 155 is maintained along the centerline of the outer sleeve window 158 since the outer sleeve 140 typically comprises return electrode 260. The position of electrode 155 in FIG. 3B is termed herein a "centerline default position". If the cutting member 145 and electrode 155 were rotated so as to be close to an edge 262*a* or 262*b* of window 158 in outer sleeve 140, RF current could arc between the electrodes 155 and 260 and potentially cause a short circuit disabling the probe. Therefore, a robust and reliable stop mechanism is required which is described next.

As can be understood from FIGS. 1 and 2A-2B, the controller 165 can always determine in real time the rotational position of drive coupling 150 and therefore the angular or rotational position of the ceramic cutting member 145 and electrode 155 can be determined. A controller algorithm can further calculate the rotational angle of the electrode 155 away from the centerline default position as the Hall sensor 245 can sense lessening of magnetic field strength as a magnet 255*a* or 255*b* in the drive coupling 150 rotates the electrode 155 away from the centerline default position. Each magnet has a specified, known strength and the algorithm can use a look-up table with that lists fields strengths corresponding to degrees of rotation away from the default position. Thus, if the Hall signal responsive to the rotated position of magnet 255*a* or 255*b* drops a specified amount from a known peak value in the centerline default position, it means the electrode 155 has moved away from the center of the window 158. In one variation, if the electrode 155 moves a selected rotational angle away from the centerline position during RF energy delivery to the electrode, the algorithm turns off RF current instantly and alerts the physician by an aural and/or visual signal, such as an alert on the LCD screen 170 on handpiece 104 and/or on a screen on a controller console (not shown). The termination of RF current delivery thus prevents the potential of an electrical arc between electrode 155 and the outer sleeve electrode 260.

It can be understood that during use, when the electrode 155 is in the position shown in FIG. 3B, the physician may be moving the energized electrode over tissue to ablate or coagulate tissue. During such use, the cutting member 145 and electrode 155 can engage or catch on tissue which inadvertently rotate the electrode 155 out of the default centerline position. Therefore, the system provides a controller algorithm, herein called an "active electrode monitoring" algorithm, wherein the controller continuously monitors position signals generated by Hall sensor 245 during RF energy delivery in both an ablation mode and a coagulation mode to determine if the electrode 155 and inner sleeve member 142 have been bumped off the centerline position. In a variation, the controller algorithms can be configured to then re-activate the motor drive 105 to move the inner sleeve member 142 and electrode 155 back to the default centerline position sleeve if electrode 155 had been bumped off the centerline position. In another variation, the controller algorithms can be configured to again automatically deliver RF current to RF electrode 155 when it is moved back to the to the default centerline position. Alternatively, the controller 165 can require the physician to manually re-start the delivery of RF current to the RF electrode 155 when it is moved back to the to the centerline position. In an aspect of the invention, the drive coupling 150 and thus magnets 255*a* and 255*b* are attached to inner sleeve member 142 and cutting member 145 in a predetermined angular relationship relative to longitudinal axis 128 so that the Hall sensor generates signals responsive to magnets 255*a*, 255*b* is the same for all probes within a probe type to thus allow the controller algorithm to function properly.

Figure 8:
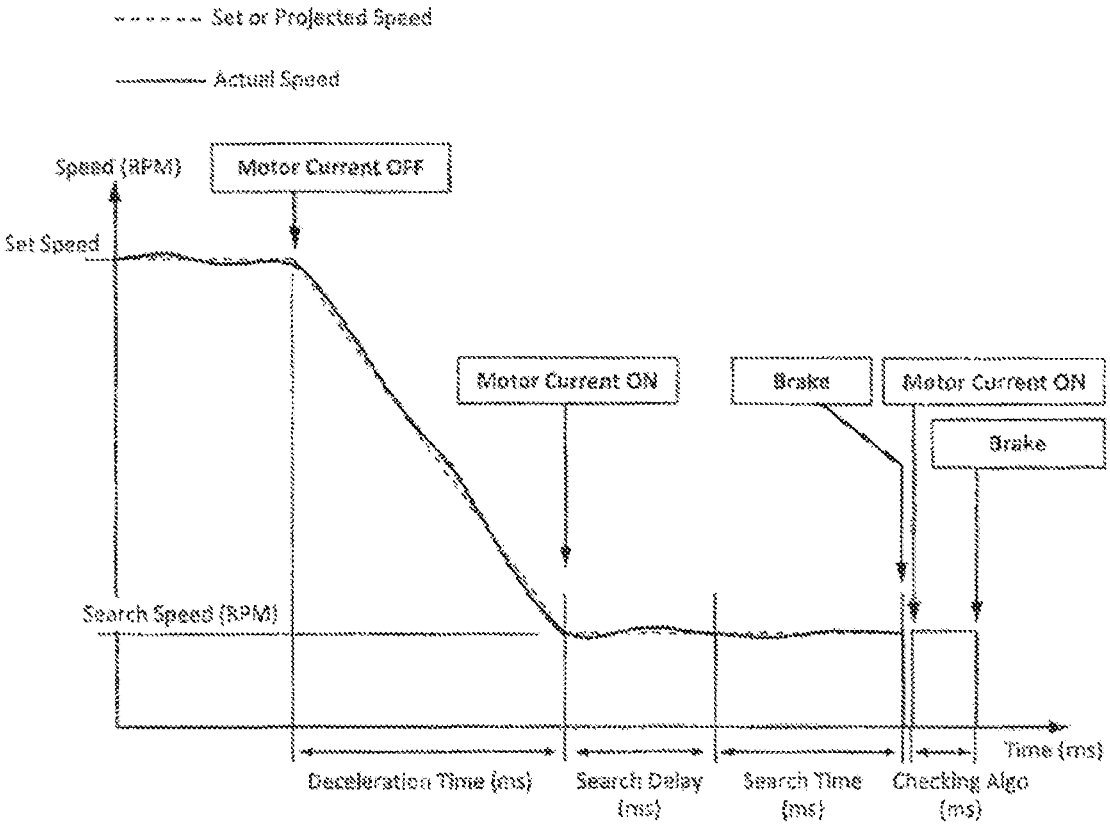
FIG. 8 is a chart relating to set speeds for a probe with a rotating cutting member as in FIGS. 1 and 3A that schematically shows the method used by a controller algorithm for stopping rotation of the cutting member in a selected default position.

Now turning to the stop mechanism or algorithms for stopping movement of a motor-driven component of working end 112, FIG. 8 schematically illustrates the algorithm and steps of the stop mechanism. In one variation, referring to FIG. 8, the stop mechanism corresponding to the invention uses (i) a dynamic braking method and algorithm to stop the rotation of the inner sleeve member 142 and cutting member 145 (FIGS. 1, 3A-3B) in an initial position, and thereafter (ii) a secondary checking algorithm is used to check the initial stop position that was attained with the dynamic braking algorithm, and if necessary, the stop algorithm can re-activate the motor drive 105 to slightly reverse (or move forward) the rotation of drive coupling 150 and inner sleeve member 142 as needed to position the cutting member 145 and electrode 155 within at the centerline position or within 0° to 5° of the targeted centerline default position. Dynamic braking is described further below. FIG. 8 schematically illustrates various aspects of controller algorithms for controlling the rotational speed of the cutting member and for stopping the cutting member 145 in the default centerline position.

In FIG. 8, it can be understood that the controller 165 is operating the probe 110 of FIGS. 1 and 3A-3B at a "set speed" which may be a PID controlled, continuous rotation mode in one direction or may be an oscillating mode where the motor drive 105 rotates the cutting member 145 in one direction and then reverses rotation as is known in the art. At higher rotational speeds such as 1,000 RPM to 20,000 RPM, it is not practical or feasible to acquire a signal from Hall sensor 245 that indicates the position of a magnet 255*a* or 255*b* in the drive coupling 150 to apply a stop algorithm. In FIG. 8, when the physician stop cutting with probe 110 by releasing actuation of an actuator button or foot pedal, current to the motor drive 105 is turned off. Thereafter, the controller algorithm uses the Hall sensor 245 to monitor deceleration of rotation of the drive coupling 150 and inner sleeve member 142 until a slower RPM is reached. The deceleration period may be from 10 ms to 1 sec and typically is about 100 ms. When a suitable slower RPM is reached which is called a "search speed" herein (see FIG. 8), the controller 165 re-activates the motor drive 105 to rotate the drive coupling at a low speed ranging from 10 RPM to 1,000 RPM and in one variation is between 50 RPM and 250 RPM. An initial "search delay" period ranging from 50 ms to 500 ms is provided to allow the PID controller to stabilize the RPM at the selected search speed. Thereafter, the controller algorithm monitors the Hall position signal of magnet strength and when the magnet parameter reaches a predetermined threshold, for example, when the rotational position of drive coupling 150 and electrode 155 correspond to the centerline default position of FIG. 3B, the control algorithm then applies dynamic braking to instantly stop rotation of the motor drive shaft 151, drive coupling 150 and the motor-driven component of the probe FIG. 8 further illustrates that the controller can check the magnet/drive coupling 150 position after the braking and stopping steps. If the Hall position signal indicates that the motor-driven component is out of the targeted default position, the motor drive 105 can be re-activated to move the motor-driven component and thereafter the brake can be applied again as described above.

Dynamic braking as shown schematically in FIG. 8 may typically stop the rotation of the drive coupling 150 with a variance of up to about 0°-15° of the targeted stop position, but this can vary even further when different types of tissue are being cut and impeding rotation of the cutting member 145, and also depending on whether the physician has completely disengaged the cutting member from the tissue interface when the motor drive is de-activated. Therefore, dynamic braking alone may not assure that the default or stop position is within a desired variance.

As background, the concept of dynamic braking is described in the following literature: https://www.ab.com/support/abdrives/documentation/techpapers/RegenOverview01.pdf and http://literature.rockwellautomation.com/idc/groups/literature/documents/wp/drives-wp004-en-p.pdf. Basically, a dynamic braking system provides a chopper transistor on the DC bus of the AC PWM drive that feeds a power resistor that transforms the regenerative electrical energy into beat energy. The heat energy is dissipated into the local environment. This process is generally called dynamic braking with the chopper transistor and related control and components called the chopper module and the power resistor called the dynamic brake resistor. The entire assembly of chopper module with dynamic brake resistor is sometimes referred to as the dynamic brake module. The dynamic brake resistor allows any magnetic energy stored in the parasitic inductance of that circuit to be safely dissipated during the turn off of the chopper transistor.

The method is called dynamic braking because the amount of braking torque that can be applied is dynamically changing as the load decelerates. In other words, the braking energy is a function of the kinetic energy in the spinning mass and as it declines, so does the braking capacity. So the faster it is spinning or the more inertia it has, the harder you can apply the brakes to it, but as it slows, you run into the law of diminishing returns and at some point, there is no longer any braking power left.

In another aspect of the invention, a method has been developed to increase the accuracy of the stopping mechanism which is a component of the positioning algorithm described above. It has been found that each magnet in a single-use probe may vary slightly from its specified strength. As described above, the positioning algorithm uses the Hall effect sensor 245 to continuously monitor the field strength of magnets 255*a* and 255*b* as the drive coupling 150 rotates and the algorithm determines the rotational position of the magnets and drive coupling based on the field strength, with the field strength rising and falling as a magnet rotates past the Hall sensor. Thus, it is important for the algorithm to have a library of fields strengths that accurately correspond to degrees of rotation away from a peak Hall signal when a magnet is adjacent the sensor 245. For this reason, an initial step of the positioning algorithm includes a "learning" step that allow the controller to learn the actual field strength of the magnets 255*a* and 255*b* which may vary from the specified strength. After a new single-use probe 110 (FIG. 1) is coupled to the handpiece 104, and after actuation of the motor drive 105, the positioning algorithm will rotate the drive coupling at least 180° and more often at least 360° while the Hall sensor 245 quantifies the field strength of the particular probe's magnets 255*a* and 255*b*. The positioning algorithm then stores the maximum and minimum Hall signals (corresponding to North and South poles) and calibrates the library of field strengths that correspond to various degrees of rotation away from a Hall min-max signal position when a magnet is adjacent the Hall sensor.

In general, a method of use relating to the learning algorithm comprises providing a handpiece with a motor drive, a controller, and a probe with a proximal hub configured for detachable coupling to the handpiece, wherein the motor drive is configured to couple to a rotating drive coupling in the hub and wherein the drive coupling carries first and second magnets with North and South poles positioned differently relative to said axis, and coupling the hub to the handpiece, activating the motor drive to thereby rotate the drive coupling and magnets at least 180°, using a handpiece sensor to sense the strength of each magnet, and using the sensed strength of the magnets for calibration in a positioning algorithm that is responsive to the sensor sensing the varying strength of the magnets in the rotating drive coupling to thereby increase accuracy in calculating the rotational position of the drive coupling 150.

Another aspect of the invention relates to an enhanced method of use using a probe working end with an electrode, such as the working end 112 of FIGS. 1 and 3B. As described above, a positioning algorithm is used to stop rotation of the electrode 155 in the default centerline position of FIG. 3B. An additional "slight oscillation" algorithm is used to activate the motor drive 105 contemporaneous with RF current to the electrode 155, particularly an RF cutting waveform for tissues ablation. The slight oscillation thus provides for a form of oscillating RF ablation. The slight oscillation algorithm rotates the electrode 155 in one direction to a predetermined degree of rotation, which the controller algorithms determine from the Hall position signals. Then, the algorithm reverses direction of the motor drive to rotate in the opposite direction until Hall position signals indicate that the predetermined degree of rotation was achieved in the opposite direction away from the electrode's default centerline position. The predetermined degree of angular motion can be any suitable rotation that is suitable for dimensions of the outer sleeve window, and in one variation is from 1° to 30° in each direction away from the centerline default position. More often, the predetermined degree of angular motion is from 5° to 15° in each direction away from the centerline default. The slight oscillation algorithm can use any suitable PID controlled motor shaft speed, and in one variation the motor shaft speed is from 50 RPM to 5,000 RPM, and more often from 100 RPM to 1,000 RPM. Stated another way, the frequency of oscillation can be from 20 Hz to 2,000 Hz and typically between 40 Hz and 400 Hz.

While the above description of the slight oscillation algorithm is provided with reference to electrode 155 on a rotating cutting member 145 of FIG. 3B, it should be appreciated that a reciprocating electrode 212 as shown in the working end 200C of FIG. 6 end could also be actuated with slight oscillation. In other words, the hook shape electrode 212 of FIG. 6 could be provided with a frequency of oscillation ranging from 20 Hz to 2,000 Hz and typically between 40 Hz and 400 Hz.

Figure 9A:
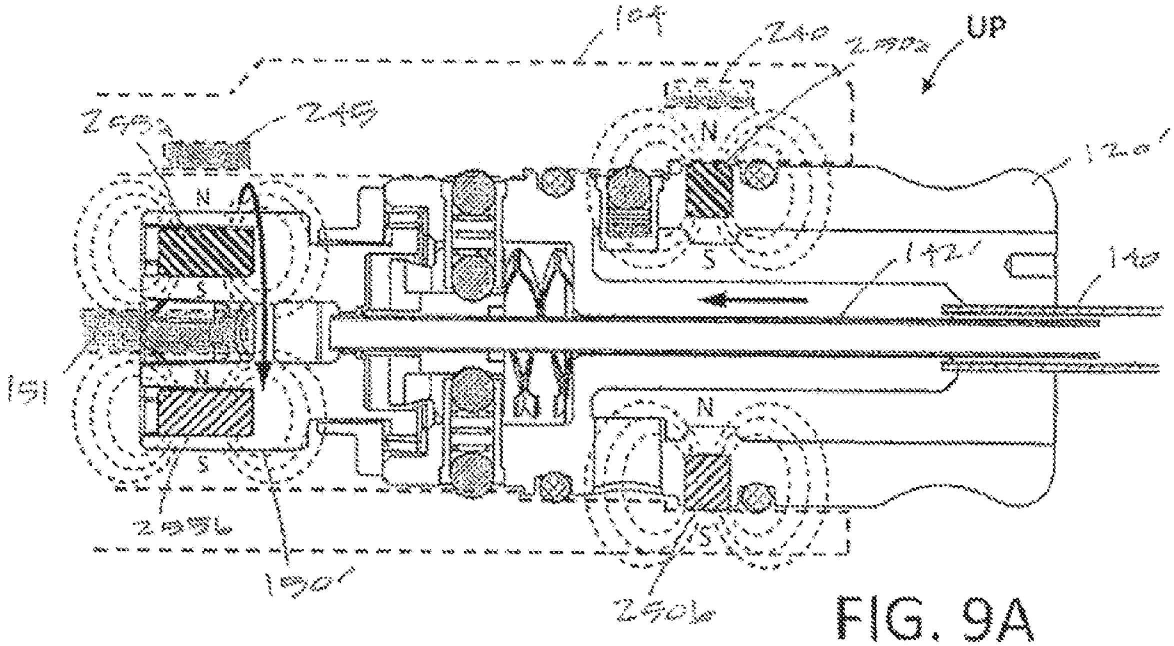
FIG. 9A is a longitudinal sectional view of a probe hub that is similar to that of FIG. 2A, except the hub of FIG. 9A has an internal cam mechanism for converting rotational motion to linear motion to axially reciprocate an electrode as in the working end of FIG. 5, wherein FIG. 9A illustrated the magnets in the hub and drive coupling are the same as in FIG. 2A and the hub is in an upward facing position relative to the handpiece.
Figure 9B:
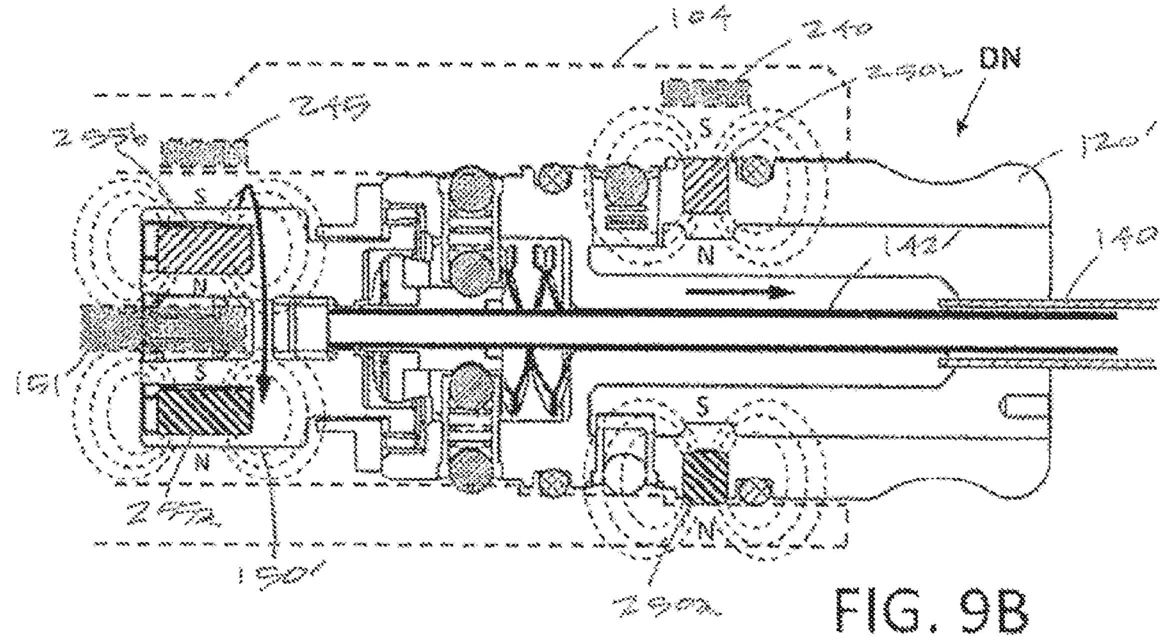
FIG. 9B is a sectional view of the hub of FIG. 9A rotated 180° in a downward facing position relative to the handpiece.

FIGS. 9A-9B are longitudinal sectional views of a probe hub 120' that corresponds to the working end 200B of FIG. 5 which has a reciprocating electrode 210. In FIGS. 9A-9B, the handpiece 104 and Hall affect sensors 240 and 245 are of course the same as described above as there is no change in the handpiece 104 for different types of probes. The probe hub 120' of FIGS. 9A-9B is very similar to the hub 120 of FIGS. 2A-2B with the first and second identification/orientation magnets 250*a* and 250*b* being the same. The third and fourth rotation al position magnets 255*a* and 255*b* also are the same and are carried by drive coupling 150'. The probe hub 120' of FIGS. 9A-9B only differs in that the drive coupling 150 rotates with a cam mechanism operatively coupled to inner sleeve member 142' to convert rotational motion to linear motion to reciprocate the electrode 210 in working end 200B of FIG. 5. A similar hub for converting rotational motion to linear motion is provided for the working ends 200C and 200D of FIGS. 6 and 7, respectively, which each have a reciprocating component (212, 218) in its working end.

Figure 10:
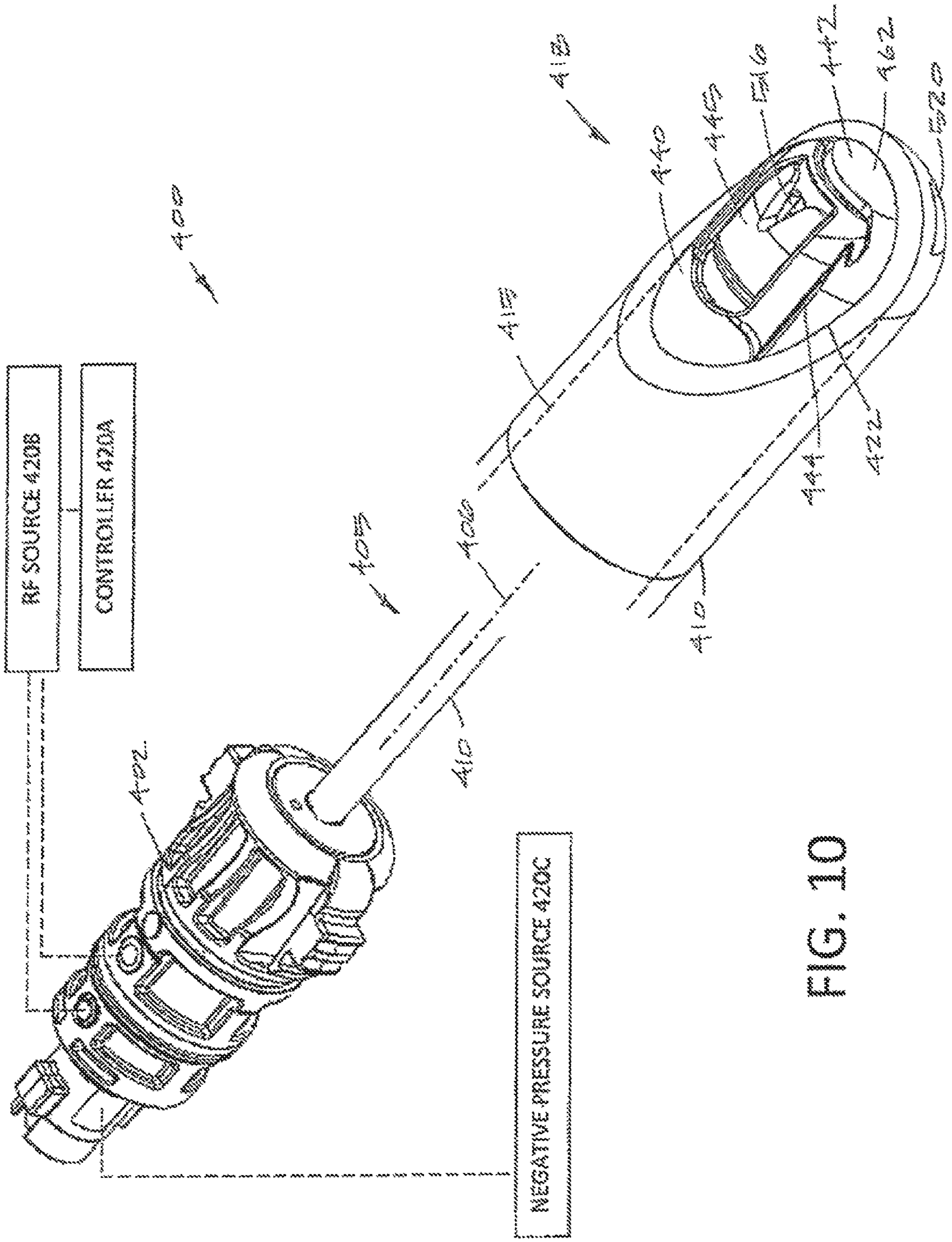
FIG. 10 is a perspective view of another variation of a probe that shows a motor-driven, rotating inner cutting sleeve that includes a longitudinal dielectric member coupled to a longitudinal conductive metal portion, wherein the dielectric member carries an active electrode and the longitudinal conductive metal portion comprises a return electrode.
Figure 11:
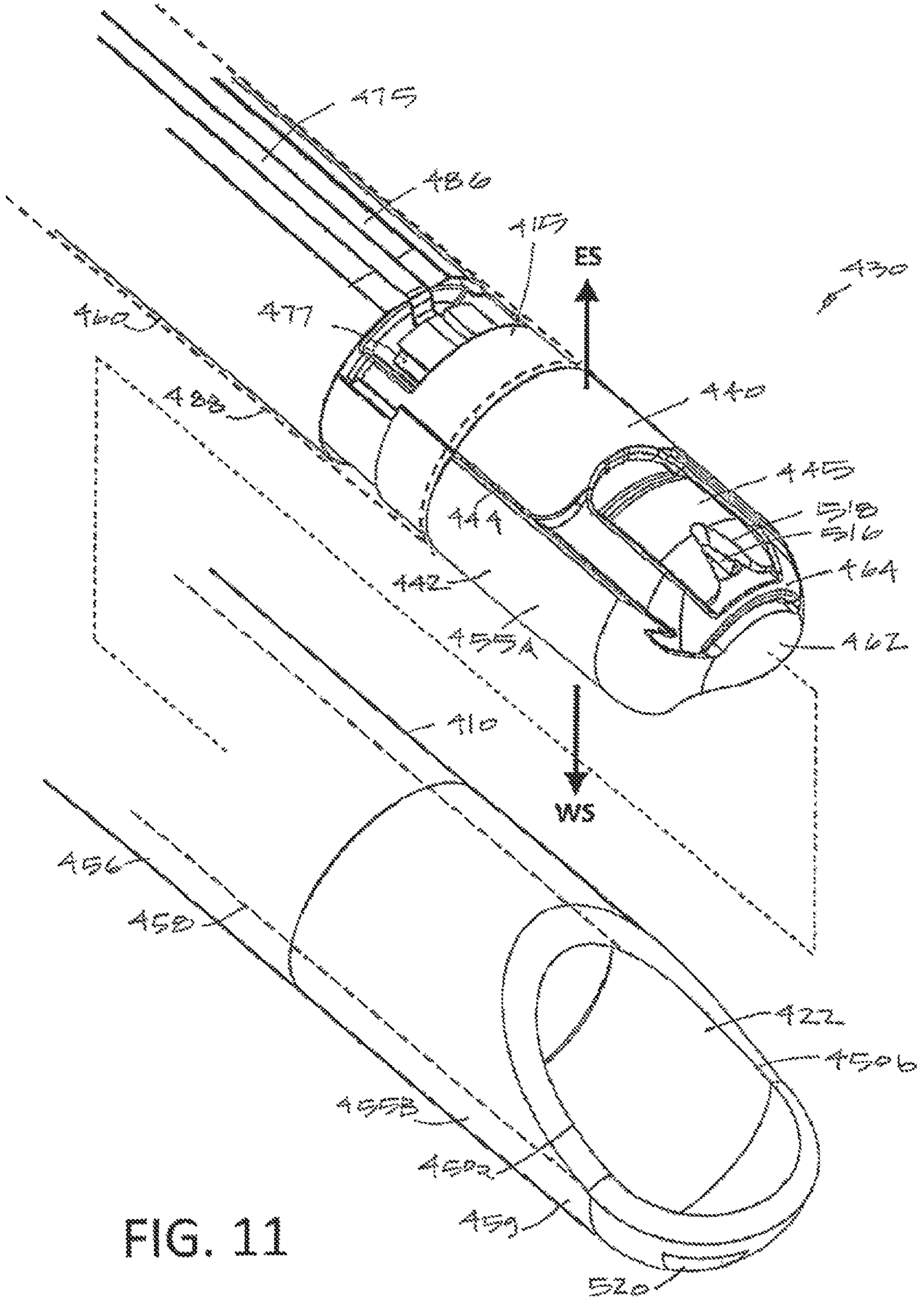
FIG. 11 is an enlarged perspective view of the working end of FIG. 10 with the inner sleeve member separated from the outer sleeve.
Figure 12:
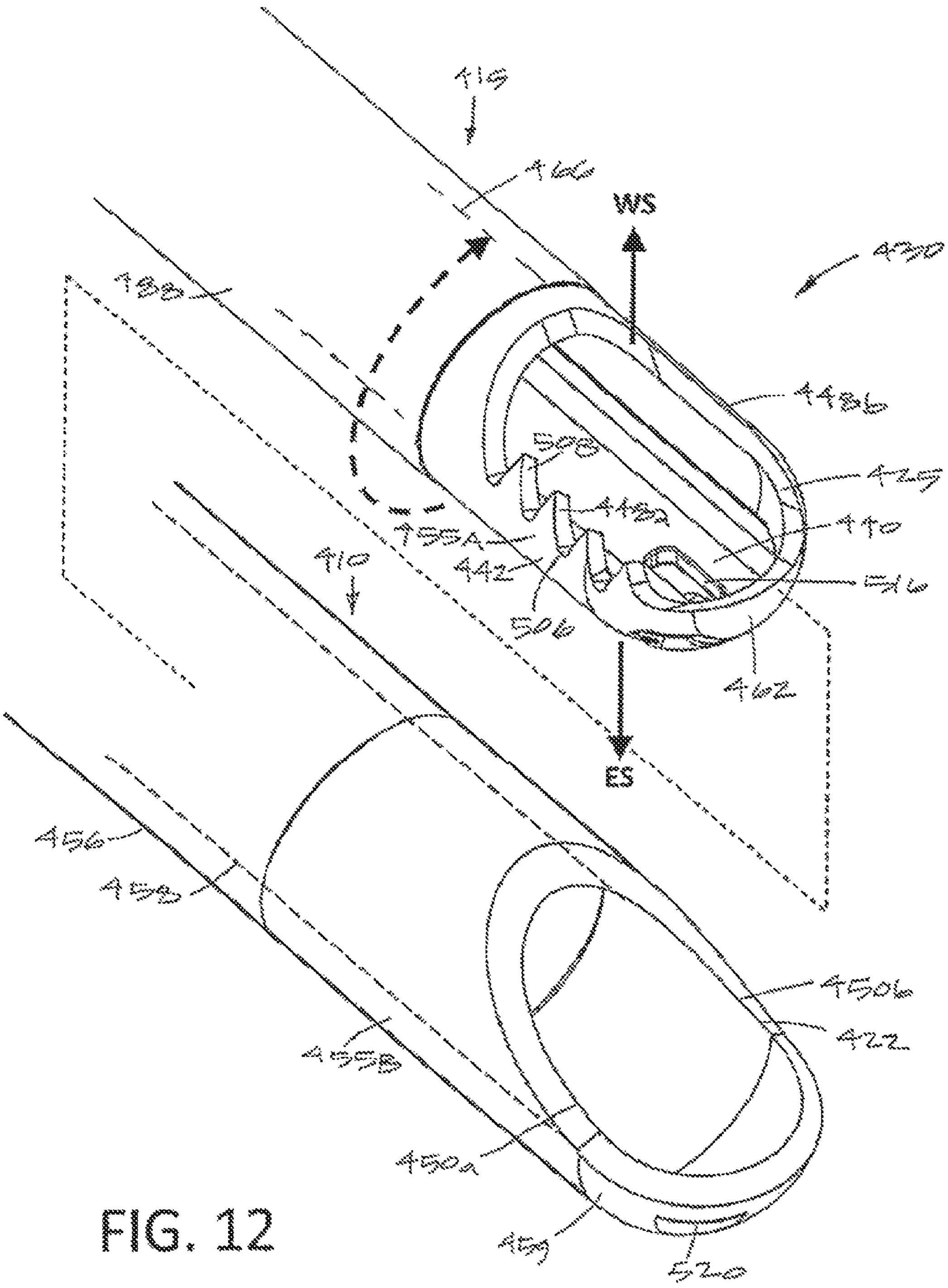
FIG. 12 is a perspective view of the working end as in FIG. 11 with the inner sleeve member rotated 180°.

Now turning to FIGS. 10, 11 and 12, another variation of an arthroscopic shaver or resection probe 400 is shown which somewhat similar to that of FIGS. 1, 2 and 3A-3B which comprises a tubular cutter having a proximal hub 402 coupled to an elongated shaft assembly 405 that extends about central longitudinal axis 406. The shaft assembly comprises an outer sleeve assembly 410 and a co-axial or concentric inner sleeve member 415 that extends to a distal or a working end 418. The hub 402 again is adapted for coupling to a handpiece and motor drive controlled by a controller 420A. The controller 420A further controls the RF source 420B and negative pressure source 420C as described previously. The controller 420A includes algorithms having the features described in previous embodiments for rotating the inner sleeve member 415 as well as stopping the inner sleeve member 415 in a selected rotational position, such as a window-closed or window-open position. The distal or working end 418 again has an outer sleeve resecting window 422 in the outer sleeve assembly 410 that cooperates with an inner sleeve member resecting window 425 (FIG. 12) in the inner sleeve member 415 for engaging and resecting tissue.

The variation or probe 400 in FIGS. 10, 11 and 12 differs from previous embodiments in that the inner sleeve member 415 of the distal or working end 418 (FIGS. 11, 12) that consists of a combination of a first longitudinal member comprising a dielectric structure or body 440, typically formed as an insert, coupled to a second longitudinal member comprising a conductive structure or portion 442, typically a generally tubular structure having an axial channel to receive the dielectric insert. The dielectric member 440 can be a ceramic or glass material and the longitudinal conductive structure 442 typically is stainless steel or other conductive metal. When assembled, the dielectric member 440 and longitudinal conductive structure 442 have longitudinal surfaces that contact one another along an interface 444 which is important for reasons described in more detail below.

As can be seen in FIG. 11, which shows components of the inner sleeve member 415 separated, the longitudinal dielectric member 440 carries an active electrode 445 which may be also may be referred to as a "first polarity" electrode herein. For convenience, the side of the inner sleeve member 415 that carries the electrode 445 is called the electrode side ES and the opposing side which carries inner window 425 is called the window side WS. Referring to FIG. 12, the inner sleeve resecting window 425 has circumferentially spaced apart first and second cutting edges 448*a* and 448*b* that are sharp for mechanically resecting tissue as such cutting edges 448*a*, 448*b* shear tissue when rotating or rotationally oscillating adjacent the cutting edges 450*a* and 450*b* of the outer sleeve window 422. In one variation shown in FIG. 12, the first and second cutting edges 448*a* and 448*b* are asymmetric with cutting teeth on one side and without such teeth on the opposing side. It should be appreciated that any types of symmetric or asymmetric edges are possible, such as serrated, linear, configured with teeth, etc.

Of particular interest, the longitudinal conductive metal structure 442 comprises a first return electrode 455A (which also may be termed a "second polarity" electrode herein) which cooperates with the first polarity or active electrode 445 to deliver energy to tissue. As will be described below, a distal portion the outer sleeve 410 comprises a second return electrode 455B. The active electrode 445 and return electrodes 455A and 455B are operatively coupled to RF source 420B and controller 420A. The outer sleeve assembly 410 has a conductive metal outer tubular member 456 with axial bore 458 therein that extends proximally to the hub 402 and distally to the distal end portion or housing 459 that carries the outer sleeve window 422. The inner sleeve member 415 has a co-axial conductive metal inner tubular member 460 that extends proximally to the hub 402 and extends distally to couple to the assembly of the longitudinal dielectric member 440 and the longitudinal metal structure 442. The co-axial metal inner tubular member 460 rotates in the axial bore 458 of the outer tubular member 456.

As can be seen best in FIGS. 12 and 14, the longitudinal metal structure 442 has dual functions in that the carries the inner cutting window 425 with circumferentially spaced-apart first and second cutting edges 448*a* and 448*b* and also functions as return electrode 455A when in a window-closed position of FIG. 10, as will be described further below.

Figure 15:
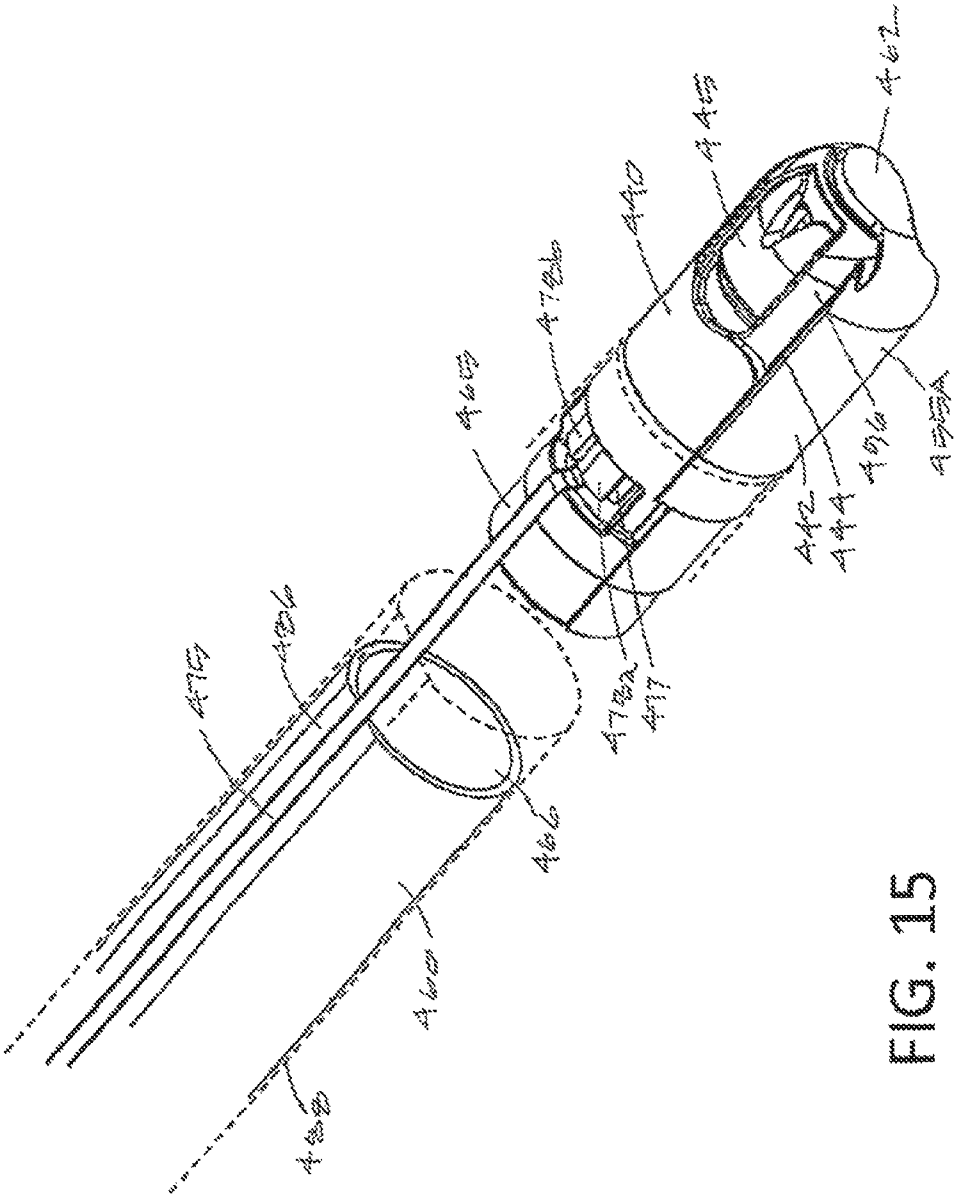
FIG. 15 is a perspective and partly assembled view of the working end of FIGS. 10-14 showing electrical connections therein.

Now referring to FIG. 12, the inner sleeve member 415 again is shown separated from the outer sleeve assembly 410 and is rotated 180° so that the electrode side ES faces downward and the window side WS is in an upward position. It can be seen that the longitudinal metal structure 442 carries the inner resecting window 425. Further, the longitudinal metal structure 442 extends distally around the tip portion 462 of the inner sleeve member 415 to thus provide substantial hoop strength as the tip portion 462 distally surrounds the longitudinal dielectric member 440 on opposing sides of the distal end 464 of the dielectric member 440. As can be seen in FIG. 15, the proximal end 465 of the assembly of the longitudinal dielectric member 440 and the longitudinal metal structure 442 is dimensioned for insertion into the axial channel or axial bore 466 of the thin wall tubular sleeve 460 to complete the structural components of the inner sleeve member 415. Thus, it can be seen how the tubular sleeve 460 with axial channel or axial bore 466 therein slides over and engages with the longitudinal dielectric member 440 and longitudinal metal structure 442 to provide a strong connection around the proximal end 465 of the components. As can best be seen in FIG. 13, the lateral sides 470*a* and 470*b* of the longitudinal dielectric member 440 are configured to slide into receiving recesses or grooves 472*a* and 472*b* on either side of the open axial channel 474 in the longitudinal metal structure 442 to thereby lock the two components 440 and 442 together.

Figure 13:
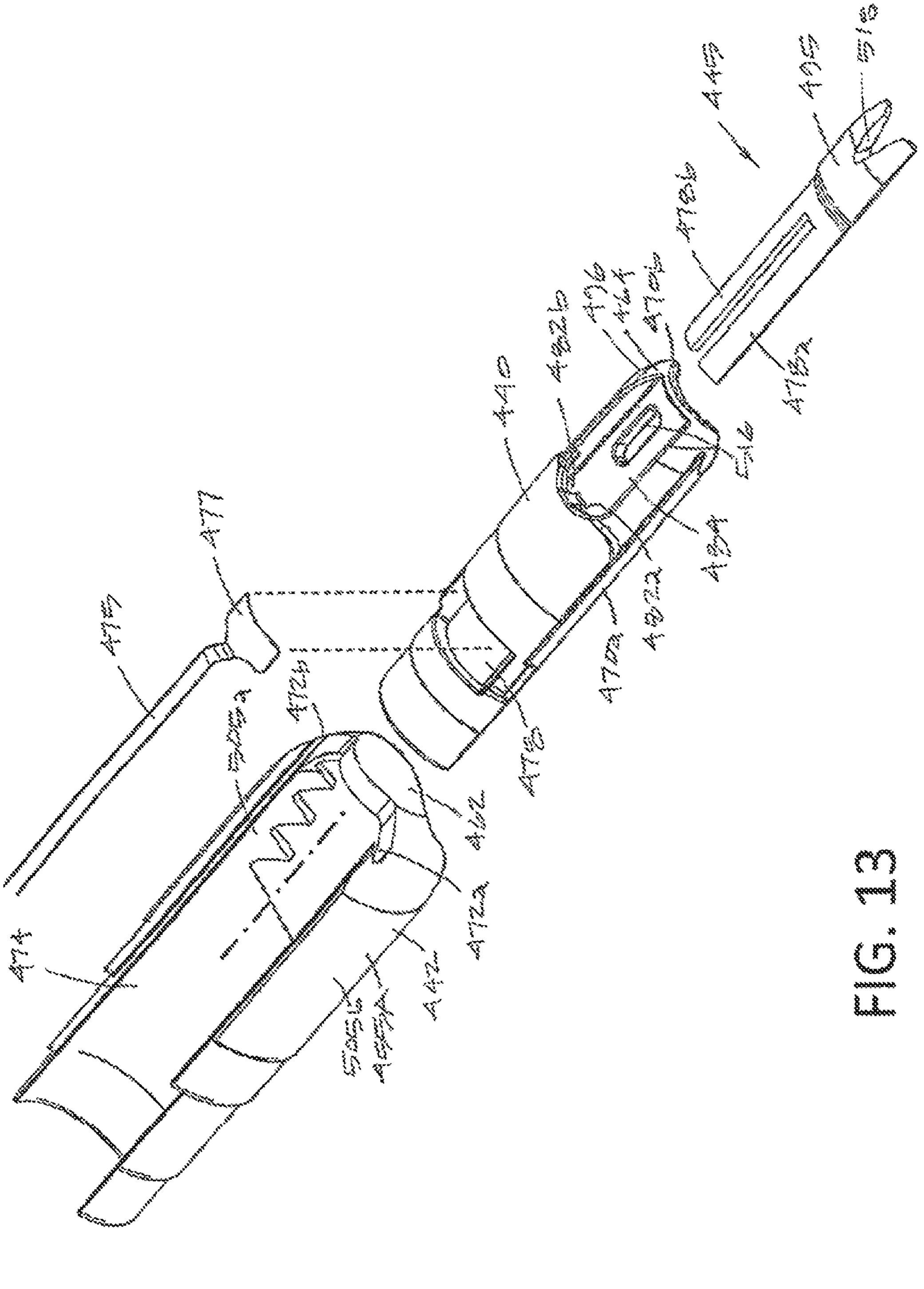
FIG. 13 is a perspective view of the working end of the probe of FIG. 10 in an exploded view showing the components thereof.
Figure 14:
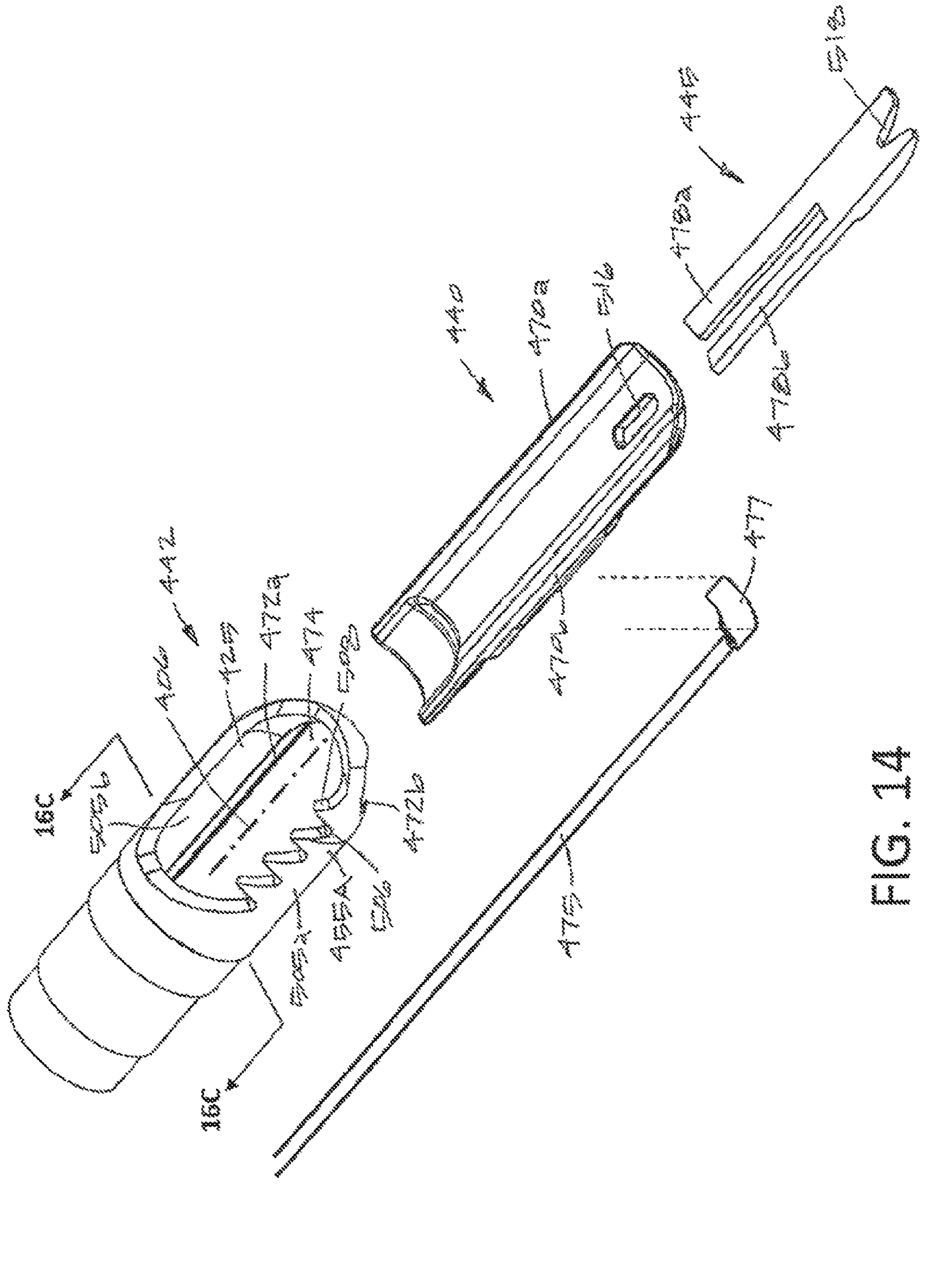
FIG. 14 is a perspective exploded view of the working end as in FIG. 13 rotated 180° to show another side of the components thereof.

FIG. 14 shows the exploded view of the components of FIG. 13 rotated 180° degrees to again show the lateral sides 470*a*, 470*b* of the dielectric member 440 configured for insertion into the receiving grooves 472*a*, 472*b* on either side of the axial channel 474 in the longitudinal metal structure 442.

Now turning to FIGS. 13 and 15, the electrical connections to the active electrode 445 and return electrodes 455A, 455B can be described. In the exploded view of FIG. 13, it can be seen that an elongated electrical lead 475 is adapted to extend longitudinally over the inner tubular member 460 (FIG. 15) to a pad portion 477 that is bendable and adapted to be inserted into a pad recess 478 in the longitudinal dielectric member 440. The electrical lead 475 is covered with an insulator (not shown) except for the pad portion 477. As can be easily understood, the active electrode 445 comprises a metal such as stainless steel, tungsten or any other suitable conductive metal with first and second legs 478*a* and 478*b* that are adapted for insertion through receiving channels 482*a* and 482*b* in the dielectric member 440 which extend into the pad recess 478. Thus, it can be understood that the electrode 445 is cantilevered over a grooved portion 484 of the dielectric member 440 distally from the dual receiving channels 482*a* and 482*b* in the dielectric member 440. The pad 477 of the electrical lead 475 then is placed in the contact with the legs 478*a* and 478*b* of the electrode 445 and soldered or otherwise electrically coupled in the recess 478. Finally, a potting material (not shown) is used to cover and fill in over the electrical pad 477 and the recess 478. Further, referring to FIG. 15, it can be seen that tubular member 460 has a flattened surface 486 for accommodating the electrical lead 475 as the tubular member 460 and axial channel or axial bore 466 therein slide over the proximal end 465 of the dielectric member 440 and metal portion 442. The flattened surface 486 of the tubular member 460 as seen in FIG. 15 allows an insulator layer 488 (such as a heat shrink material) shown in phantom view to cover the entirety of the tubular member 460, the insulated electrical lead 475, and the proximal and medial portions 465, 490 of the dielectric member 440 and the longitudinal metal structure 442. This describes the electrical lead 475 extending to the active electrode 445 carried within the dielectric member 440. The proximal end (not shown) of the electrical lead 475 extends into the hub 402 (FIG. 10) and thereafter connects to electrical contacts in a motor-drive handpiece which allows for rotation of the inner sleeve member 415 and for coupling electrical energy to the electrical lead 475, as described in earlier embodiments.

As described above, the longitudinal metal structure 442 of the inner sleeve member 415 (FIGS. 13, 15) comprises the first return electrode 455A. However, the inner sleeve member 415 does not carry an electrical lead to the longitudinal metal structure 442. Rather, the outer sleeve assembly 410 of FIGS. 10, 11 and 12 includes an elongate metal outer tubular member 456 that comprises an electrical conductor and is adapted to carry current from the hub 402 to the distal end or housing portion 459 of the outer sleeve assembly 410. Since the longitudinal metal structure 442 of the inner sleeve member 415 rotates with a close fit within the axial bore 458 of the outer tubular member 456, the longitudinal metal structure 442 becomes a return electrode 455A due to its contact with the outer tubular member 456. Thus, referring to FIG. 12, the longitudinal metal conductive structure 442 and the distal end housing 459 of the outer tubular member 456 comprise first and second return electrodes 455A and 455B, respectively.

Figure 16A:
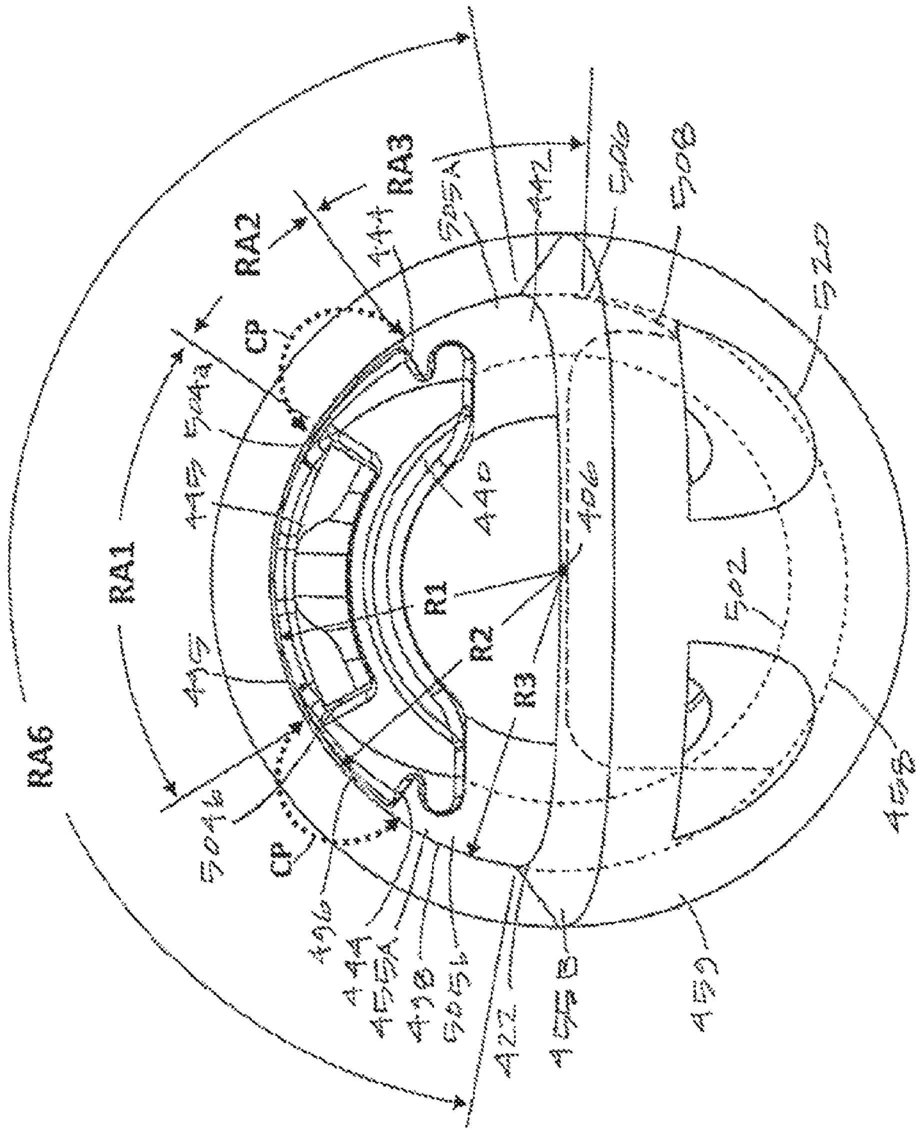
FIG. 16A is an end view of components of the working end of FIGS. 10-15 showing radial dimensions of components and features thereof.

In another aspect of the invention, referring to FIGS. 15 and 16A, the active electrode 445 is dome-shaped with a surface 495 that has a radius or curvature that is a segment of a cylindrical shape so that the outer surface 495 of the dome of the electrode 445 when viewed in a transverse sectional view (FIG. 16A) is substantially aligned with the outer cylindrical surface 496 of the dielectric member 440 and outer surface 498 of the longitudinal metal structure 442. The dome-shaped surface 495 of the electrode 445 is advantageous for contacting tissue since it projects outward as opposed to a flat-surface electrode. Further, the thicker, dome-shaped central surface of active electrode 445 results in far slower degradation and disintegration of the electrode 445 during prolonged use. The durability of active electrode 445 is important for arthroscopic procedures in which the electrosurgical components of the invention may be used for many minutes. Referring to FIG. 16A, the radius R1 of the outer surface 495 of the active electrode 445 is approximately equal to the radius R2 of the outer surface 496 of dielectric member 440. In one variation, the radius R1 of outer surface 495 of electrode 445 is smaller than radius R2 of outer surface 496 of the dielectric member 440 by 0.020" or less. Similarly, the radius R2 of the outer surface 496 of the dielectric member 440 is approximately equal to radius R3 of the outer surface 498 of the longitudinal metal structure 442. In one variation, the radius R2 of dielectric member 440 is smaller than radius R3 of metal structure 442 by 0.020" or less. These dimensions are important for providing the inner sleeve member 415 with a rotating close fit within axial bore 458 of the outer tubular member 456 and distal housing 459.

Figure 16B:
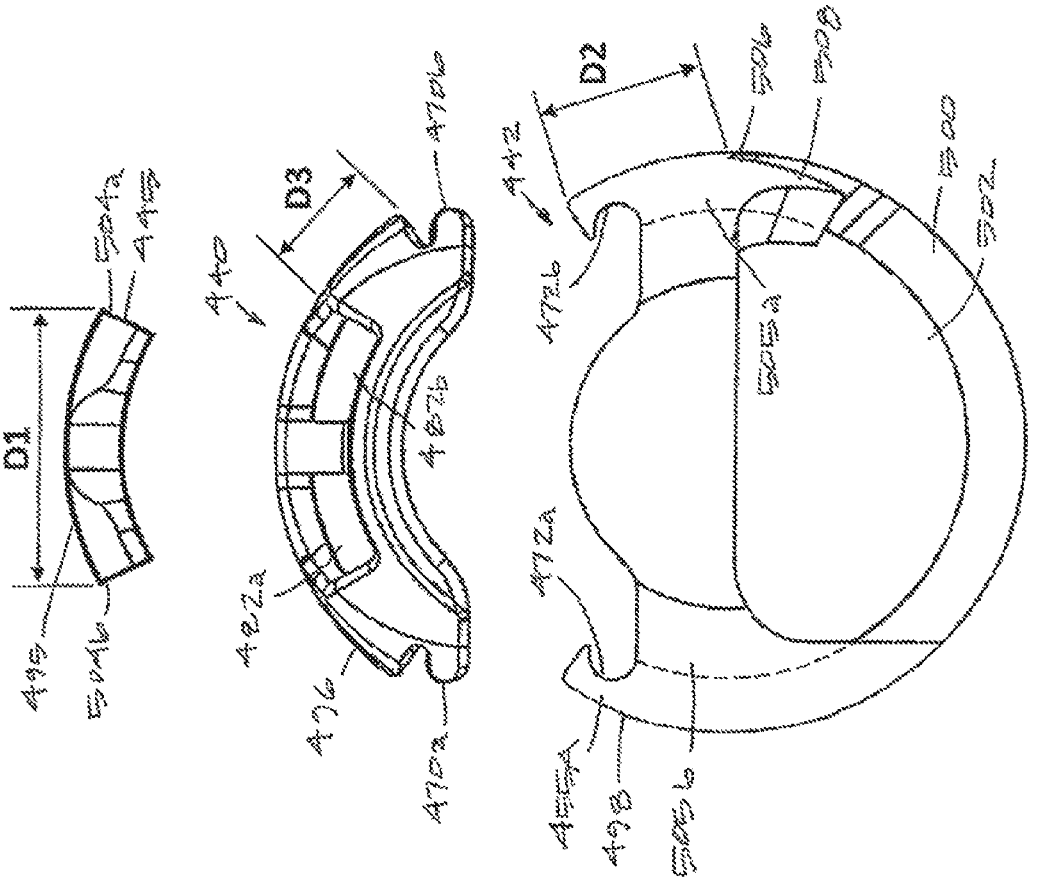
FIG. 16B is an end view of components of the working end of FIG. 1 in an exploded view.
Figure 16C:
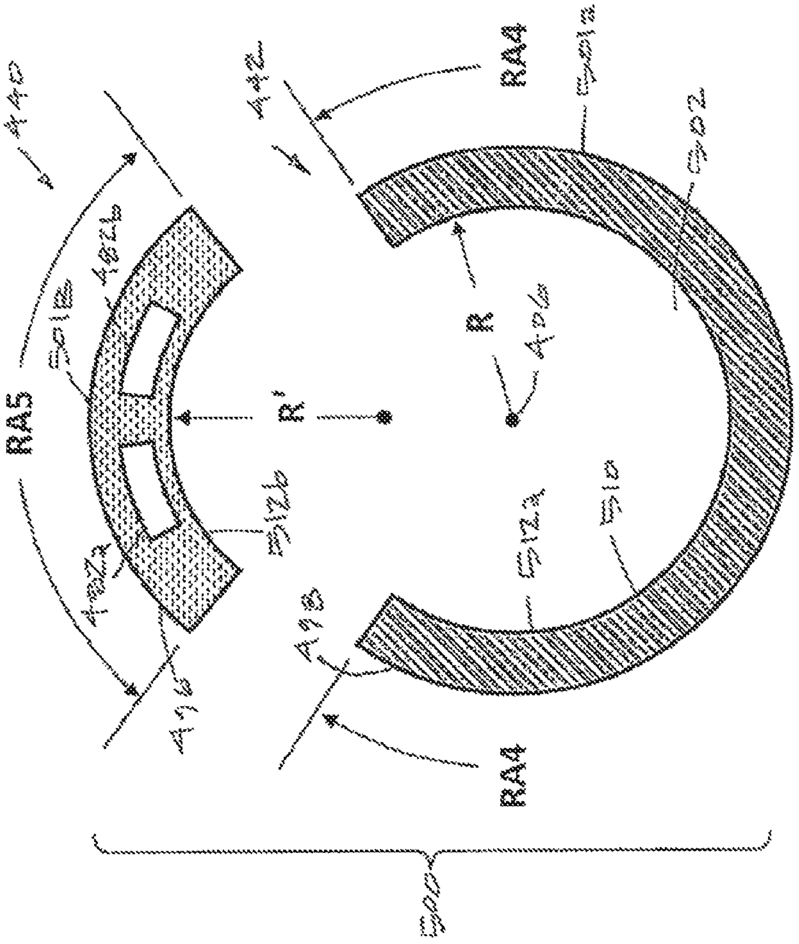
FIG. 16C is a cross-sectional view of components of the working end of FIGS. 13-14 taken along line 16C-16C of FIG. 14 rotated 90° with the components moved apart.

Referring to FIGS. 16B and 16C, in one aspect of the invention, the longitudinal dielectric member 440 is formed as a curved, annular dielectric portion. The longitudinal metal structure 442 can also be formed as a C-shaped annular portion or segment to form a wall 500 (with metal wall portion 501*a* and dielectric wall portion 501*b*) around an interior channel 502 therein that communicates within axial channel or axial bore 466 in the inner tubular member 460 and a negative pressure source 420C for aspirating tissue chips and fluid from a working space as is known in the art. The annular dielectric portion 440 can be assembled with the C-shaped annular metal portion to form a generally tubular or cylindrical distal housing.

As will be further explained below, the dimensions and orientations of several elements of the active electrode 445, the dielectric member 440 and the conductive structure 442 in relation to the outer sleeve window 422 are important. In a variation shown in FIG. 16A, the active electrode 445 has an outer surface 495 extending over a radial angle RA1 of at least 20°. Often, the outer surface 495 of electrode 445 extends over a radial angle RA1 of at least 40°. In this variation, the lateral electrode edges 504*a* and 504*b* are spaced apart from the closest aspect of metal structure 442 at interface 444 by a radial angle RA2 of at least 10° and often at least 20°. The minimum dimensional angle RA2 between the electrode edges 504*a*, 504*b* and interface 444 is needed to provide for optimal plasma ignition when using the probe in an plasma ablation mode.

FIGS. 16A and 16B also show a minimum radial angle dimension RA3 of side wall portions 505*a* and 505*b* of the conductive structure 442 that extend on either side of inner window 425. This radial angle RA3 indicates the minimum height of such wall portions 505*a*, 505*b* from the recesses 506 between teeth 508 (FIGS. 12 and 16A) to the interface 444 which provides the assembly of the dielectric member 440 and metal structure 442 with needed strength during use. As can be seen in FIG. 16A, the metal side wall portions 505*a*, 550*b* form the respective inner window cutting edges 448*a*, 448*b* and the outer surface 498 of side walls 505*a* and 505*b* extend over a radial angle at least 10° and often at least 20°.

Figure 17:
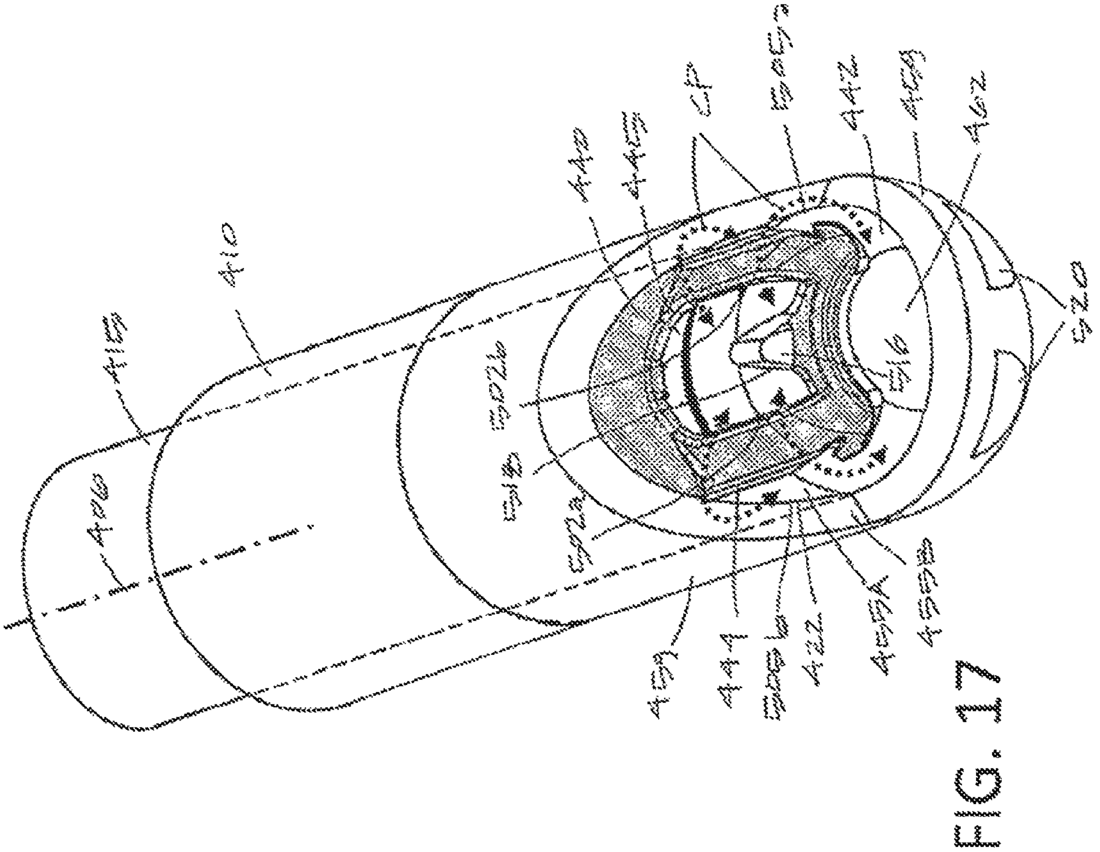
FIG. 17 is a perspective view of the working end of FIGS. 10-15 showing RF current paths between active and return electrodes.

Referring now to FIG. 16B, in another aspect of the invention, important characteristics of the active electrode 445, dielectric member 440 and longitudinal metal structure 442 can be further described by certain dimensions other that a radial angle. In one aspect, the active electrode 445 has an outer surface 495 extending circumferentially dimension D1 at least 0.030". The metal side wall portions 505*a* and 505*b* that form the edges of inner window 425 have an outer surface 498 extending circumferentially a dimension D2 of at least 0.015". Further, the lateral edges 504*a* and 504*b* of electrode 445 are spaced apart dimension D3 from the closest surface of metal structure 442 by at least 0.010". In FIG. 16B, it can be seen that dimension D3 equals the distance over the exposed surface 496 of dielectric structure 440. In FIGS. 16A-16B and 17, the active electrode 445 is shown with an outer surface 495 that is symmetric circumferentially relative to dielectric member 440 and inner window 425, but it should be appreciated that electrode 445 can be asymmetric circumferentially relative to the dielectric member 440 and/or inner window 425.

Referring now to FIG. 16C, a sectional, exploded view of dielectric member 440 and metal structure 442 is shown with the section taken proximal to window 425 (see FIG. 13). As can seen in FIG. 16C, the wall 500 has an annular metal portion 501*a* and an annular dielectric portion 501*b* extending radially around axis 406 and interior channel 502. The metal wall portion 501*a* typically will extend radially around interior channel 502 in a radial angle RA4 of at least 120° or at least 180°. When describing the metal wall portion 501*a* herein that extends in radial angle RA4 as in FIG. 16C, it is meant to refer to the metal wall portion 501*a* which is proximal to window 425. The dimension of radial angle RA4 provides the required hoop strength to the metal portion 442 and thus the distal end of the inner sleeve member. In this variation, referring to FIG. 16C, the wall 501*b* of dielectric member 440 extends radially around interior channel 502 proximal to window 425 in a radial angle RA5 of at least 45° or at least 60°.

Now turning to FIG. 17, another important aspect of the invention can be described. As can be seen in FIG. 17, the inner sleeve member 415 has been stopped from rotation in a selected rotational position wherein the active electrode 445 carried by dielectric member 440 is positioned centrally in resecting window 422 of the outer sleeve assembly 410. In this variation, it should be appreciated that the outer sleeve window 422 is shown with sharp metal cutting edges without teeth or serrations, but it should be appreciated that the outer sleeve window 422 can have any form of sharp teeth, serrations or the like and fall within the scope of the invention.

In FIG. 17, it can also be seen that the longitudinal metal structure 442 of the inner sleeve member 415 is exposed in the outer sleeve window 422 when the outer sleeve assembly 415 has been stopped in the rotational position where electrode 445 is positioned centrally in the resecting window 422. As described above, the longitudinal metal structure

442 of the inner sleeve member 415 comprises a first return electrode 455A and the distal portion of housing 459 of outer sleeve assembly 410 comprises a second return electrode 455B. FIG. 17 shows RF current paths CP that indicate the shortest path for RF current between the active electrode 445 and a return electrode when operating in conductive saline environment. As can be seen in FIG. 17, the shortest RF current paths CP are from the active electrode 445 to the longitudinal metal structure 442 (i.e., first return electrode 455A) along interface 444 of the dielectric member 440 and metal structure 442. In other words, the shortest RF current path is not from the active electrode 445 to the cutting edges 450*a* and 450*b* of the outer window 422 in distal housing 459 which comprise the second return electrode 455B. In one aspect of the invention, the location of interface 444 between dielectric member 440 and metal structure 442 in the selected stopped position (or window closed position) is critical to prevent a short current path CP to the cutting edges 450*a* and 450*b* of outer window 422 (i.e., second return electrode 455A). If substantial RF current paths were directly from electrode 445 to cutting edges 450*a* and 450*b*, the RF plasma at the cutting edges would rapidly degrade and dull such sharp edges 450*a*, 450*b*. In turn, such dull cutting edges 450*a*, 450*b* of the outer sleeve window 422 would diminish the resection rate resulting from rotating or oscillating the inner sleeve member 415 and inner window 425 in the outer sleeve window 422.

In general, a surgical a probe for resecting tissue corresponding to the invention (FIGS. 10-17) comprises an elongated shaft extending about a longitudinal axis 406 comprising co-axial outer and inner sleeve assemblies 410, 415 having respective outer and inner resecting windows 422 and 425 in distal ends thereof, wherein the inner sleeve member has (i) a longitudinal dielectric wall member that carries a first polarity or active electrode 445, and (ii) a conductive metal wall structure 442 with side wall portions 505*a* and 505*b* extending around an inner resecting window 425 that comprise a first return electrode 455A, wherein the active electrode 445 is spaced apart from the side wall portions 505*a*, 505*b* by at least 0.010" as described above.

In general, referring to FIG. 17, a tissue resecting probe corresponding to the invention comprises an elongated shaft 405 extending about a longitudinal axis 406 and further comprises co-axial outer and inner sleeve assemblies 410 and 415 having respective outer and inner resecting windows 422 and 425 in distal ends thereof, wherein inner sleeve member 415 carries a first polarity or active electrode 445 therein, and the structure around the inner window 422 comprises a second polarity or return electrode 455A. In this variation, the structure at least partially surrounding the outer window 425 comprises second polarity or return electrode.

In another aspect of the invention, again referring FIG. 17, the surgical resecting probe comprises a windowed inner sleeve member 415 rotatable within a windowed outer sleeve assembly 410 wherein a controller 420A and motor drive are adapted to rotate the inner sleeve member through window-open and window-closed positions and wherein the controller 420A is adapted to stop motor-driven rotation of the inner sleeve member in a selected position wherein the active electrode 445 is spaced apart from cutting edges 450*a* and 450*b* (i.e., the second return electrode 455B) of outer sleeve window 422 and wherein the first return electrode 455A is disposed intermediate the active electrode 445 and the cutting edges 450*a* and 450*b* of the outer sleeve window 422 (i.e., the second return electrode 455B). This aspect of the invention can be also be described by the dimensions of the surfaces of inner sleeve components relative to the outer window 422 of outer sleeve 410. As can be seen in FIG. 16A, the radial angle RA1 of the electrode 445 and the radial angles RA2 of the dielectric member 440 on both sides of the electrode can be combined to define a first radial angle, and the outer window 422 in the outer sleeve 410 defines a second radial angle indicated at RA6. In this aspect, the second radial angle RA6 is greater than combined radials angles defined by the surfaces of the electrode 445 and dielectric member 440 of the inner sleeve 415 which can be rotated and then stopped in the outer window 425 of outer sleeve 410. Typically, the radial angle RA6 of the outer window 422 is at least 90° or at least 135°.

In another aspect of the invention, referring to FIGS. 13-15, 16A and 16C, the resecting probe 400 (FIG. 10) comprises a windowed inner sleeve member 415 rotatable within a windowed outer sleeve assembly 410 wherein a controller 420A (FIG. 10) and motor drive are adapted to rotate the inner sleeve member 415 through window-open and window-closed positions, wherein a distal portion of the inner sleeve member 415 comprises a cylindrical wall 500 defining an outer surface and an inner surface 510 around interior channel 502 therein (see FIGS. 16A, 16C). In FIG. 16C, it can be seen that interior channel 502 is surrounded by a first wall portion 501*a* with inner surface 512*a* of metal structure 442 and a second wall portion 501*b* with inner surface 512*b* of the longitudinal dielectric member 440 and wherein each of the first and second wall portions 501*a* and 501*b* comprise the full thickness of the cylindrical wall 500 and provide the structural strength of the wall. This aspect of the invention allows for that maximum diameter of the interior channel 502 relative to the outer diameter of the assembly 430 wherein such a larger interior channel facilitates fluid flows and tissue chip extraction. The above-described means of assembling the wall 500 is this preferred over having a wall that is layered, for example with a metal inner sleeve and dielectric outer sleeve or partial sleeve to carry the electrode. As can be seen in FIG. 16C, the radii R and R' of the inner surfaces 512*a* and 512*b*, respectively, are approximately the same dimension. Again, it should be appreciated that the term “wall” 500 as used herein describes the metal wall structure proximal to window 425 or dielectric structure opposing the window.

In FIGS. 10-15, it can be seen that the dielectric member 440 has a port 516 therein that lies under a v-notch 518 in the electrode 445. The port 516 is adapted for aspiration of fluid therethrough during RF energy delivery in an ablation mode which can reduce bubbles from the vicinity of the active electrode 445 as plasma is generated. Further, FIGS. 10 and 17 show ports 520 in the distal end housing 459 of outer sleeve 410 which are adapted to provide fluid flow through the shaft assembly in a window-closed position as shown in FIGS. 10 and 17 to maintain a constant fluid outflow as opposed to a fluctuating outflow as would be the case otherwise with the inner sleeve member 415 rotating at high RPM through window-open and window-closed positions.

Figure 18:
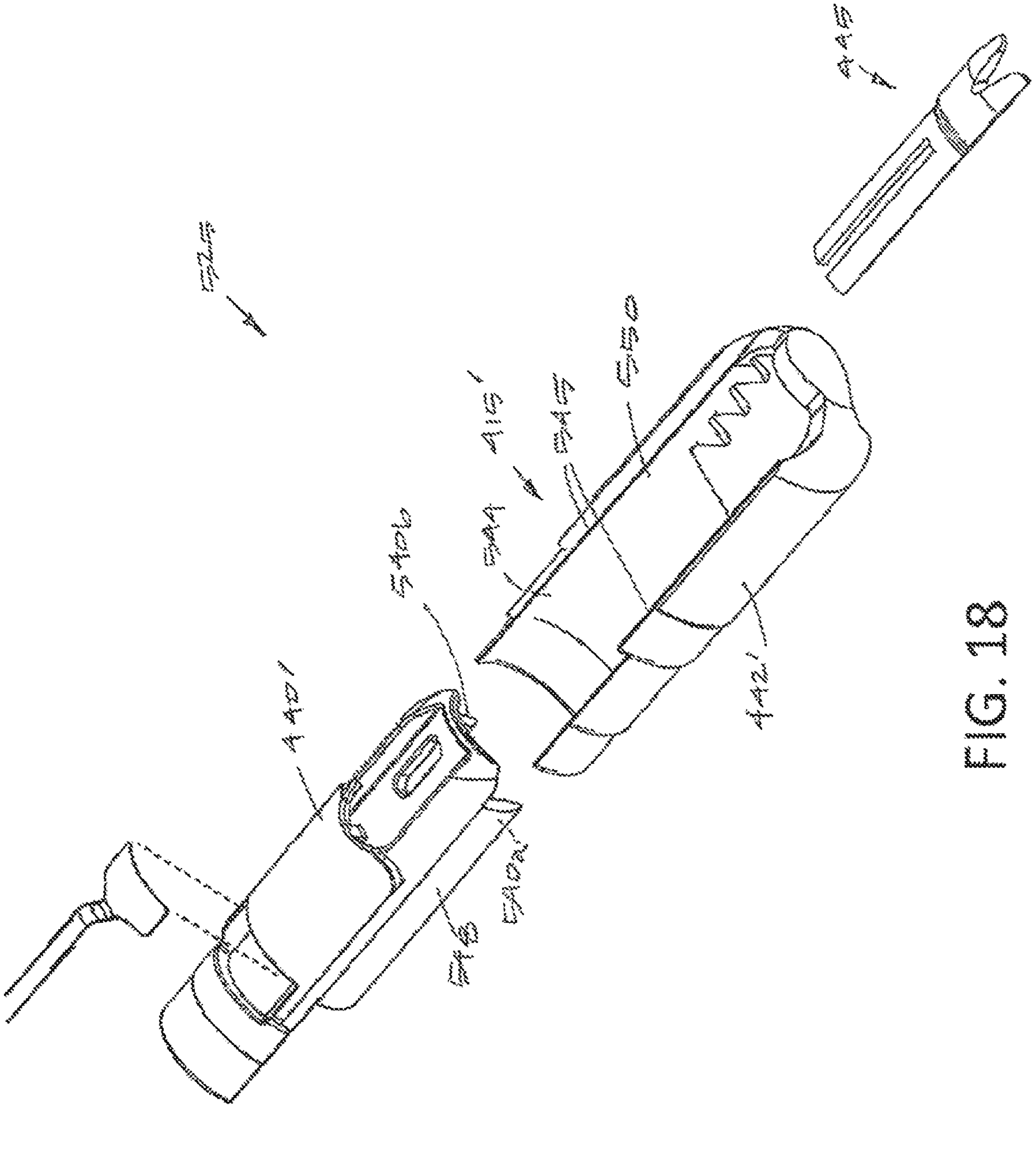
FIG. 18 is a perspective exploded view of a working end of another variation of a probe similar to that of FIG. 10 showing the components thereof.
Figure 19:
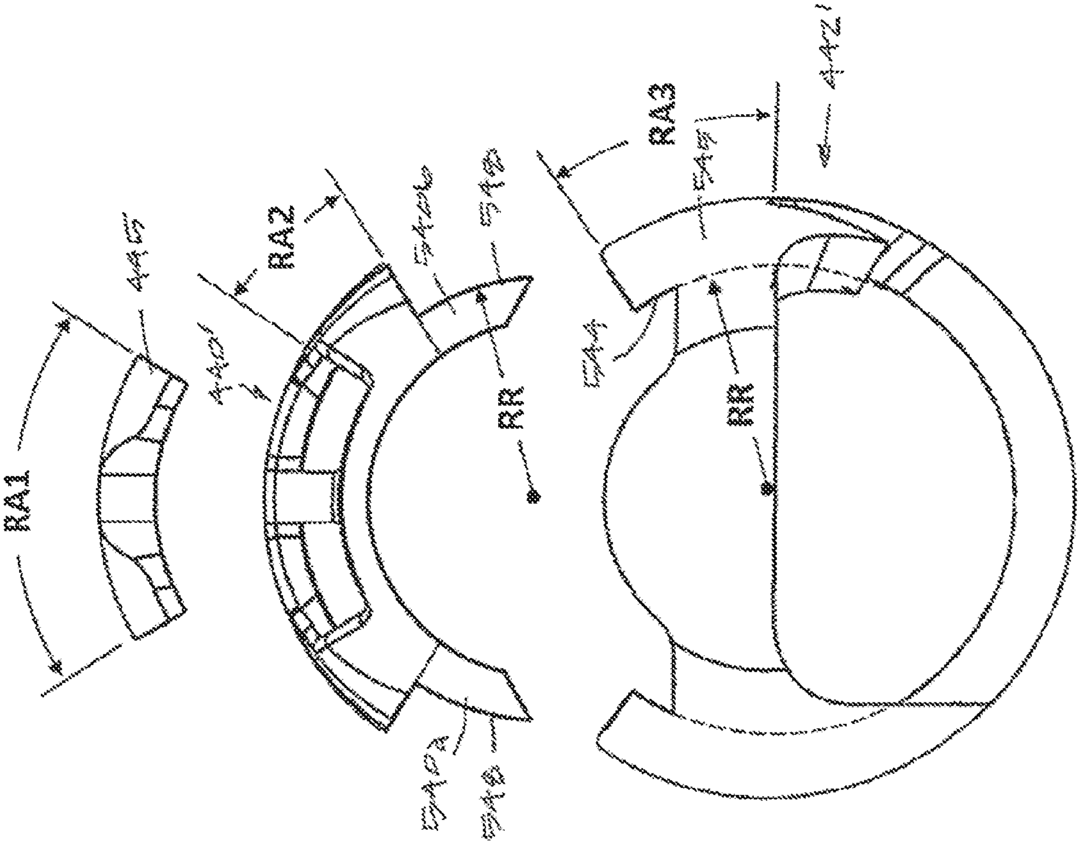
FIG. 19 is an end view of components of the working end of FIG. 18.

Now turning to FIGS. 18-19, another variation of a probe working end 525 is shown, and more particularly the distal end of the inner sleeve member 415' is shown in an exploded view and is similar to the embodiment of FIGS. 10 to 16. The variation of FIG. 18 again includes a longitudinal dielectric body 440' and a longitudinal conductive metal body 442'. This variation differs the previous embodiment shown in FIG. 13 in that the structure provided for securely coupling the components 440' and 442' together differs. As can be seen in FIGS. 18 and 19, the dielectric component

440' has lateral elements 540*a* and 540*b* extending in a part-cylindrical form that are adapted to slide into and engage the inner surfaces 544 of walls 545 of the metal longitudinal metal body portion 442'. As can be seen best in FIG. 19, the lateral elements 540*a* and 540*b* of the dielectric member 440' have an outer surface 548 with a radius RR that matches the inner surface 544 and radius RR of the metal portion 442'. Thus, it can be understood that by axially sliding and inserting the dielectric member 440' can into the longitudinal opening or channel 550 in longitudinal metal portion 442', a secure and durable connection can be provided between the dielectric and metal components 440' and 442'. In FIG. 19, the radial angle RA1 of the surface of the electrode 445, the radial angle RA2 of a portion of the dielectric member 440', and the radial angle RA3 of wall portion of the metal body 442' and the can be the same as described previously.

Figure 20:
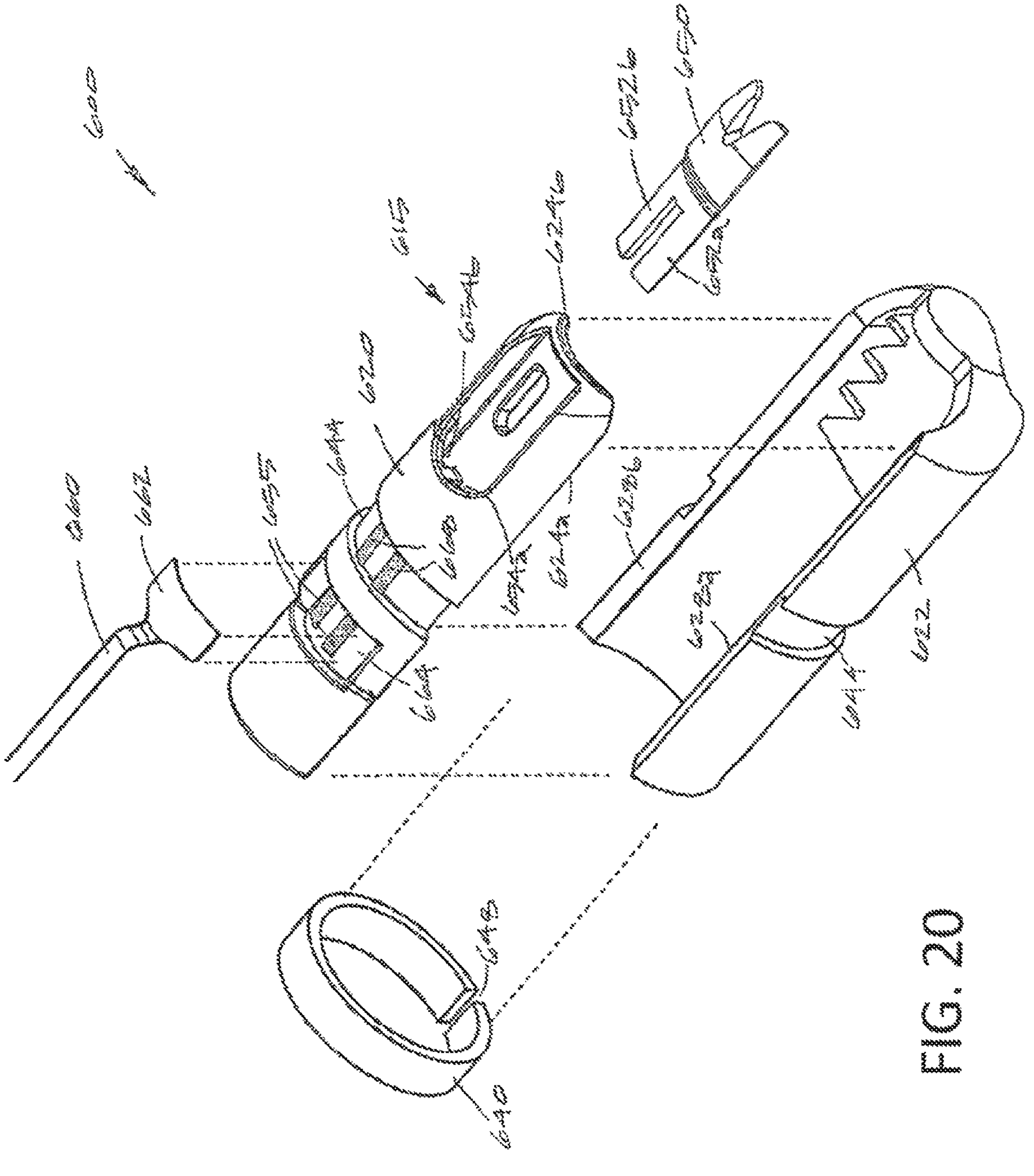
FIG. 20 is a perspective exploded view of another variation of a probe similar to that of FIGS. 10 and 18 showing the components thereof.
Figure 21:
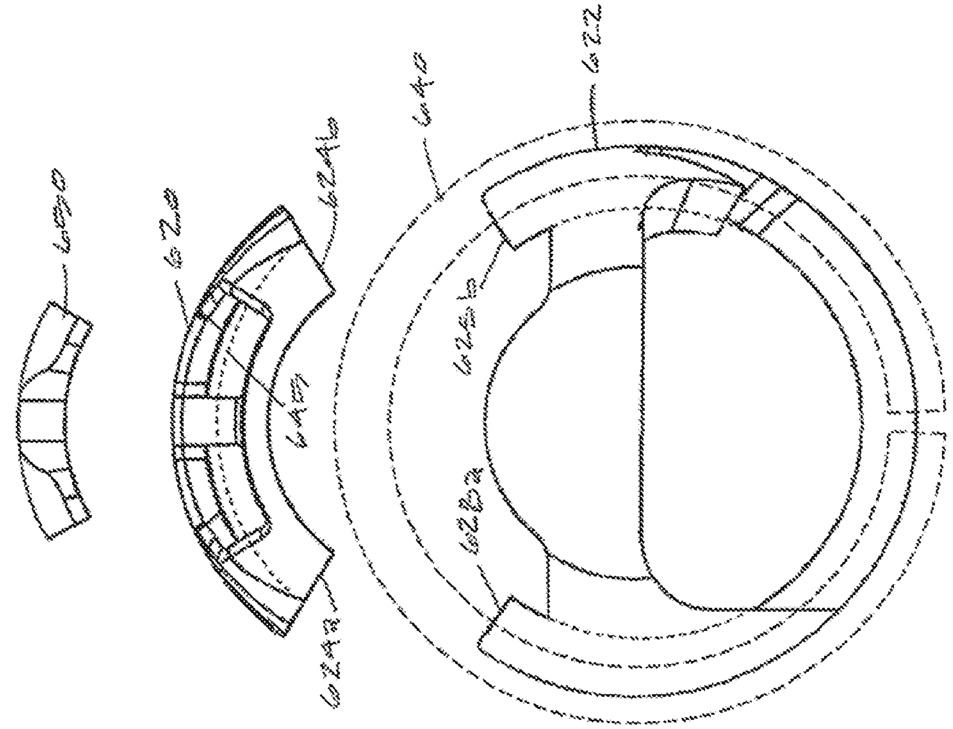
FIG. 21 is an end view of components of the working end of FIG. 20.

In FIG. 20, another variation of a working end 600 of an inner sleeve member 615 is provided in an exploded view to illustrate the structural components that are adapted to securely connect the longitudinal dielectric member 620 to the longitudinal metal body 622. In this variation, the lateral edges 624*a* and 624*b* of the dielectric member 620 do not interlock with the lateral edges 628*a* and 628*b* of the metal body 622 or overlap as in the previous variations. As can be seen in FIGS. 20 and 21, the interfaces of the lateral edges of the components 620, 622 simply abut one another and are securely fixed to one another by a retaining collar 640 that is adapted to fit into an annular notch or recess 644 in both the dielectric member 620 the metal body 622 to securely hold the components together. As can be understood, the metal retaining collar 640 can have a discontinuity or gap 648 in its circumference to allow the collar to be tensioned and slipped over the components 620 and 622 into the recess 644. Thereafter, the gap 648 in the collar 640 can be welded to thus permanently couple the dielectric and metal components 620 and 622.

In the variation shown in FIG. 20, it can be seen that an active electrode 650 with legs 652*a* and 652*b* is similar to the version described previously in FIGS. 13-15. In FIG. 20, it can be seen that the legs 652*a* and 652*b* extend into receiving channels 654*a* and 654*b* in the dielectric member 620. The electrical lead 660 in FIG. 20 again has a pad element 662 that is received by a recess 664 in the dielectric member 620 to contact electrical leads 665 therein. In this variation, the electrical leads 655 in the recess 664 are bare to make electrical contact with the pad element 662 but are coated with an insulator 668 in the location where such leads extend through the dielectric member 620 and into contact with the legs 652*a* and 652*b* of the electrode 650. In all other respects, the assembly of components in FIG. 20 functions in the same manner as described previously.

Figure 22:
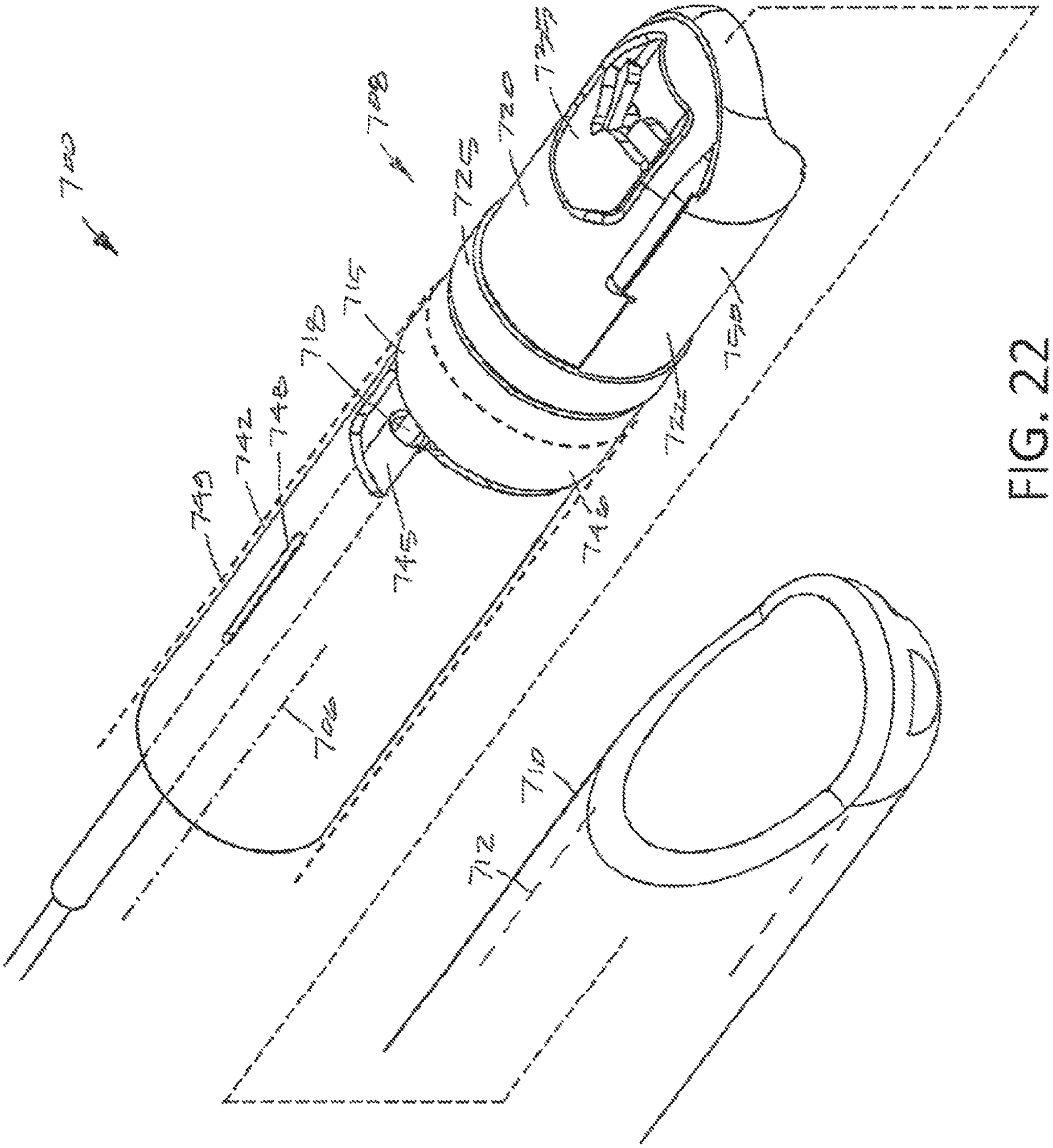
FIG. 22 is a perspective partly disassembled view of another variation of a probe similar to that of FIGS. 10 and 18 showing the components thereof.
Figure 23:
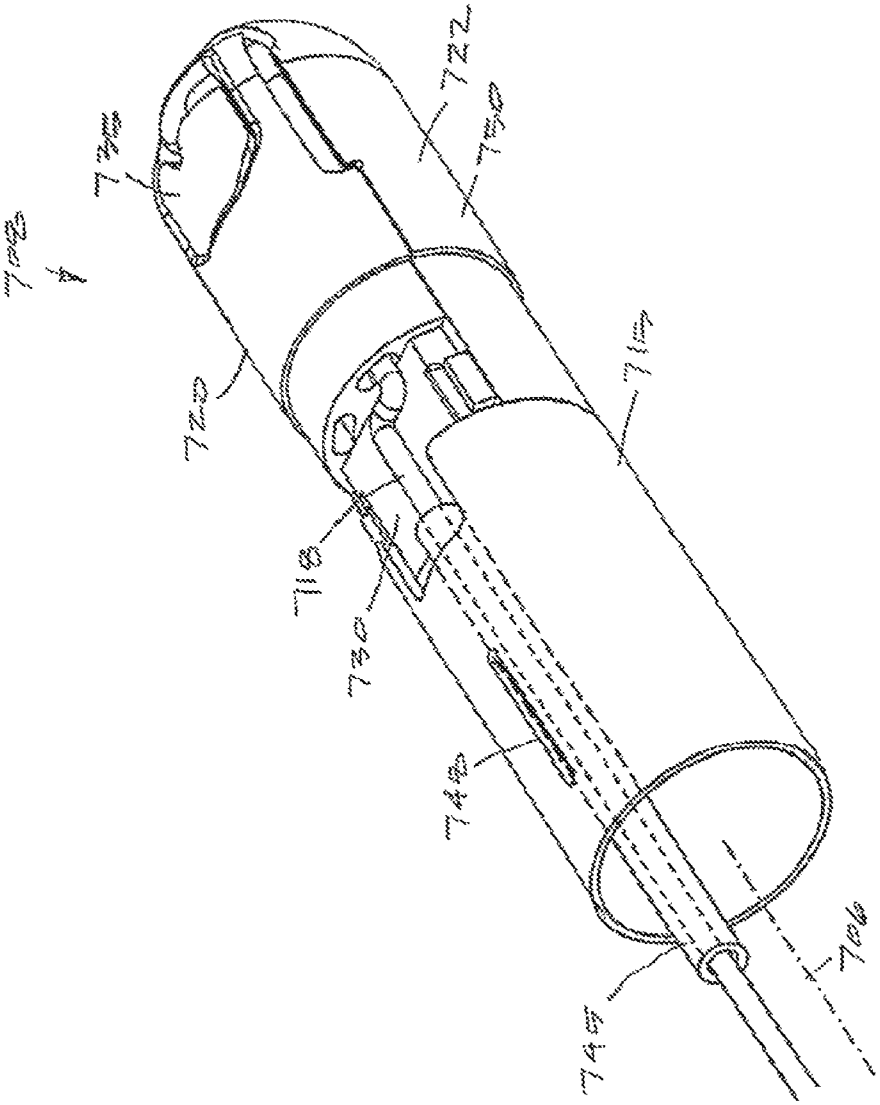
FIG. 23 is another perspective view of components of the working end of FIG. 22.

Now turning to FIGS. 22-26, another variation of probe 700 is shown with hub 702 and shaft 705 (see FIG. 25A) extending about longitudinal axis 706 to a working end 708 shown in FIG. 22. FIG. 22 shows a distal portion of the outer sleeve assembly 710 and axial bore 712 therein together with inner sleeve member 715. FIG. 23 shows the inner sleeve member 715 from a different angle to better illustrate the electrical lead 718 carried by the inner sleeve. Now turning to FIG. 24, which is an exploded view of the inner sleeve member 715, it can be seen that the longitudinal dielectric member 720 is again secured to the longitudinal metal body 722 and coupled to tubular member 724 with a retaining collar 725. Such a retaining collar 725 used to fix together the dielectric member 720 and the metal body 722 can be similar to that described in the embodiment of FIG. 20.

Figure 24:
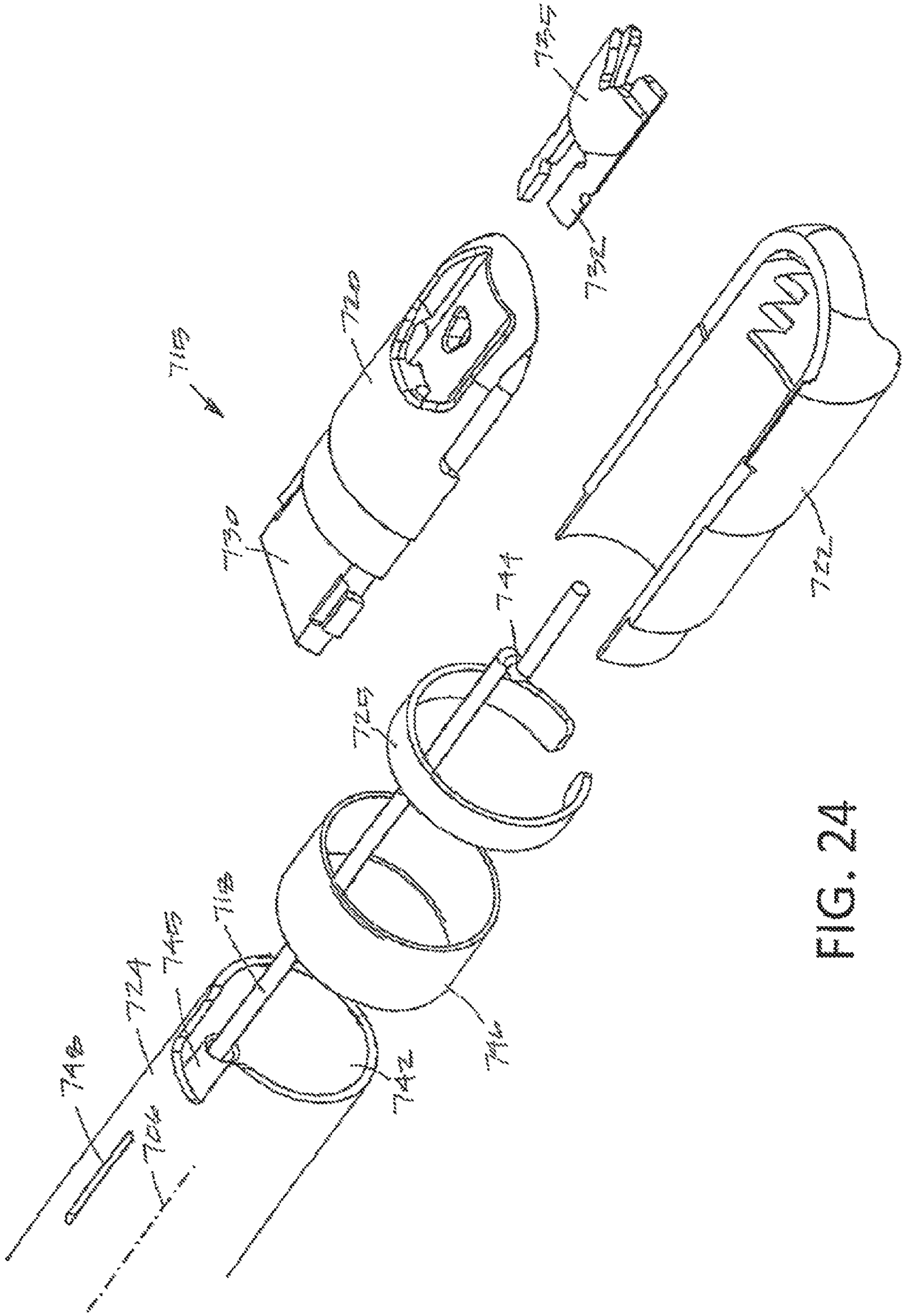
FIG. 24 is an exploded view of the component of the probe of FIGS. 22 and 23.

Referring to FIG. 24, this variation differs from previous embodiments in that the electrical lead 718 extends through a recess 730 in the dielectric member 720 and couples to a leg 732 of the active electrode 735. The electrical lead 718 is not carried on an exterior surface of tubular member 724. Instead, the electrical lead 718 extends to the active electrode 735 through the interior bore 742 of the tubular member. As can be seen in FIG. 22, the electrical lead 718 extends in the proximal direction from the electrode 735 and is flexed at bend 744 to enter the interior bore 742 of the inner tubular member 724 and in this variation extends through a hypotube 745 which is coupled to the wall of the tubular member 740. It can be seen that a slot 748 is provided in the wall of and tubular member 724 which allows for welding the hypotube 745 to the interior surface of bore 742 in the tubular member 724. At least one similar slot (not shown) can be provided along the length of the tubular member 724 to secure the hypotube 745 in place. It has been found that is important to carry the electrical lead 718 within the interior bore 742 of the tubular member 724 to protect it from potential damage. In the previous embodiments, for example the version of FIG. 15, the electrical lead 475 extended in a flat surface 486 along the outer surface of the inner tubular member 460 and was then covered with insulator layer 488. In the previous embodiment of FIG. 15, since the shaft 405 of the probe 400 (FIG. 10) could be torqued and bent significantly during a procedure, high-speed rotation of the inner sleeve member 415 had the potential of abrading and degrading the insulator sleeve 488 overlying the electrical lead 425 which could cause an electrical short. Therefore, one aspect of the invention as shown in FIGS. 22-24 includes carrying the electrical lead 718 in the interior bore 742 of the metal tubular member 724 to ensure that bending or torque on the shaft 705 while operating the inner sleeve member 715 at high RPM cannot damage the electrical lead 718. FIGS. 22 and 24 also show an annular bushing 746 that is adapted to cover the recess 730 that is filled with potting material as described previously.

Referring again to FIG. 22, a heat shrink insulator sleeve 749 covering the tubular member 724 and the at least a portion of the bushing 746. Thus, in high speed rotation, the insulator sleeve 749 and bushing 746 are the bearing surfaces of the inner sleeve member 715 as it rotates in the outer sleeve 710.

It can be appreciated from FIGS. 22-24 that the inner tubular member 724 and the hypotube 745 comprise a return electrode 750 with conductive saline flowing through the interior channel 755 of the tubular member 724. Thus, obviously the electrical lead 718 carries its own substantial insulation layer on it surface. In one variation, the electrical lead 718 is a copper wire, platinum wire or the like, instead of a stainless-steel wire since such a stainless-steel wire would be resistively heated. In an aspect of the invention, the electrical lead 718 is of a material that will not be resistively heated as this would heat saline outflows traveling through the channel 755 which would then elevate the temperature of the handpiece which is undesirable.

Figure 25A:
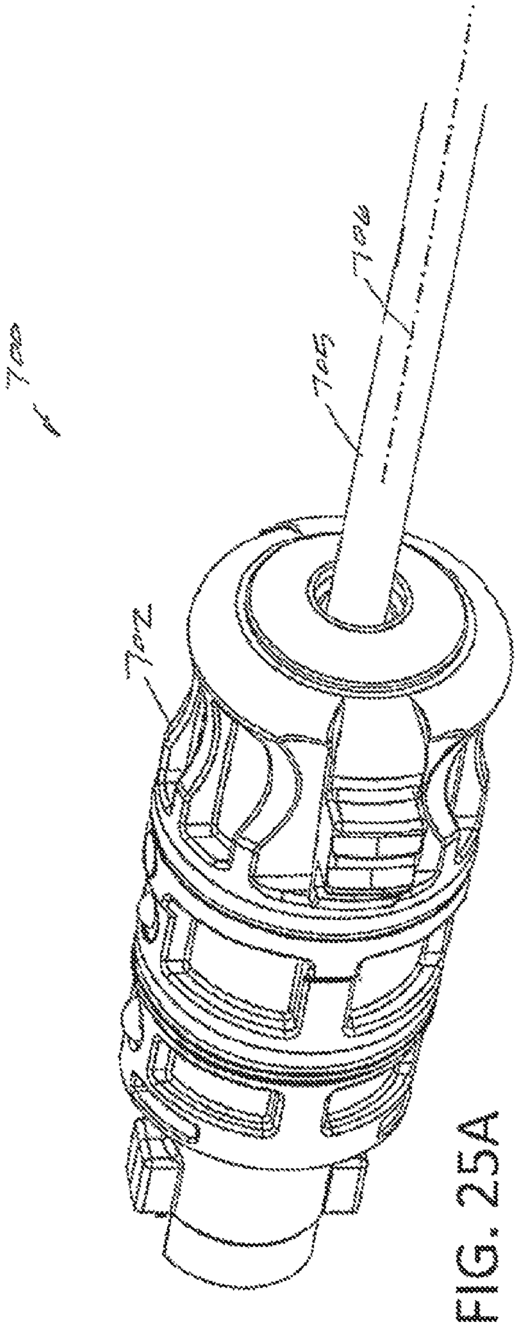
FIG. 25A is a perspective view of the probe of FIGS. 22 and 23 showing the hub and shaft of the probe.
Figure 25B:
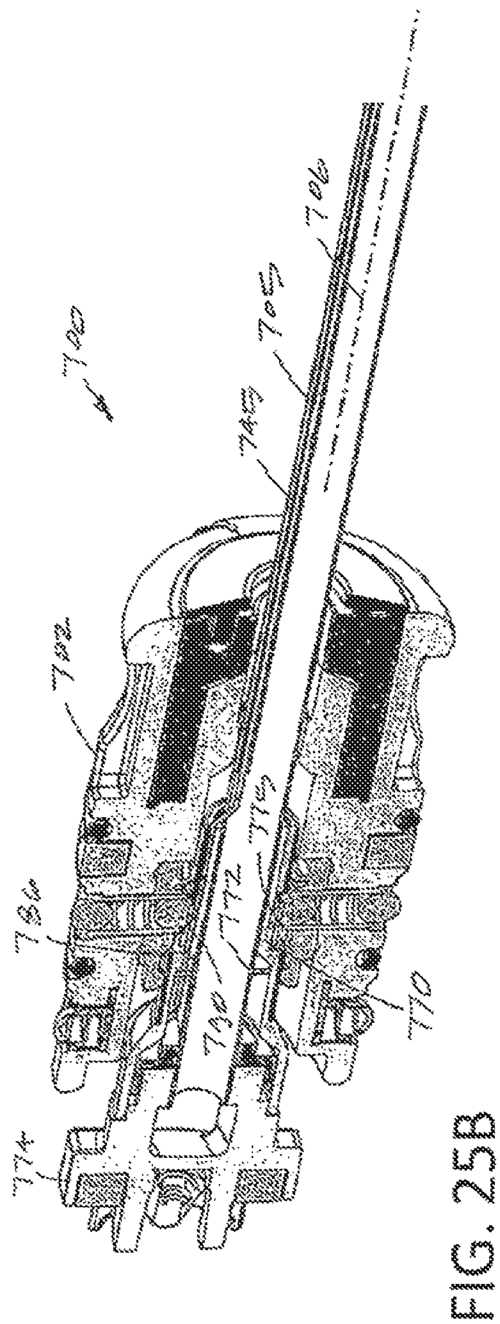
FIG. 25B is a longitudinal sectional view of the probe of FIG. 25A.
Figure 26:
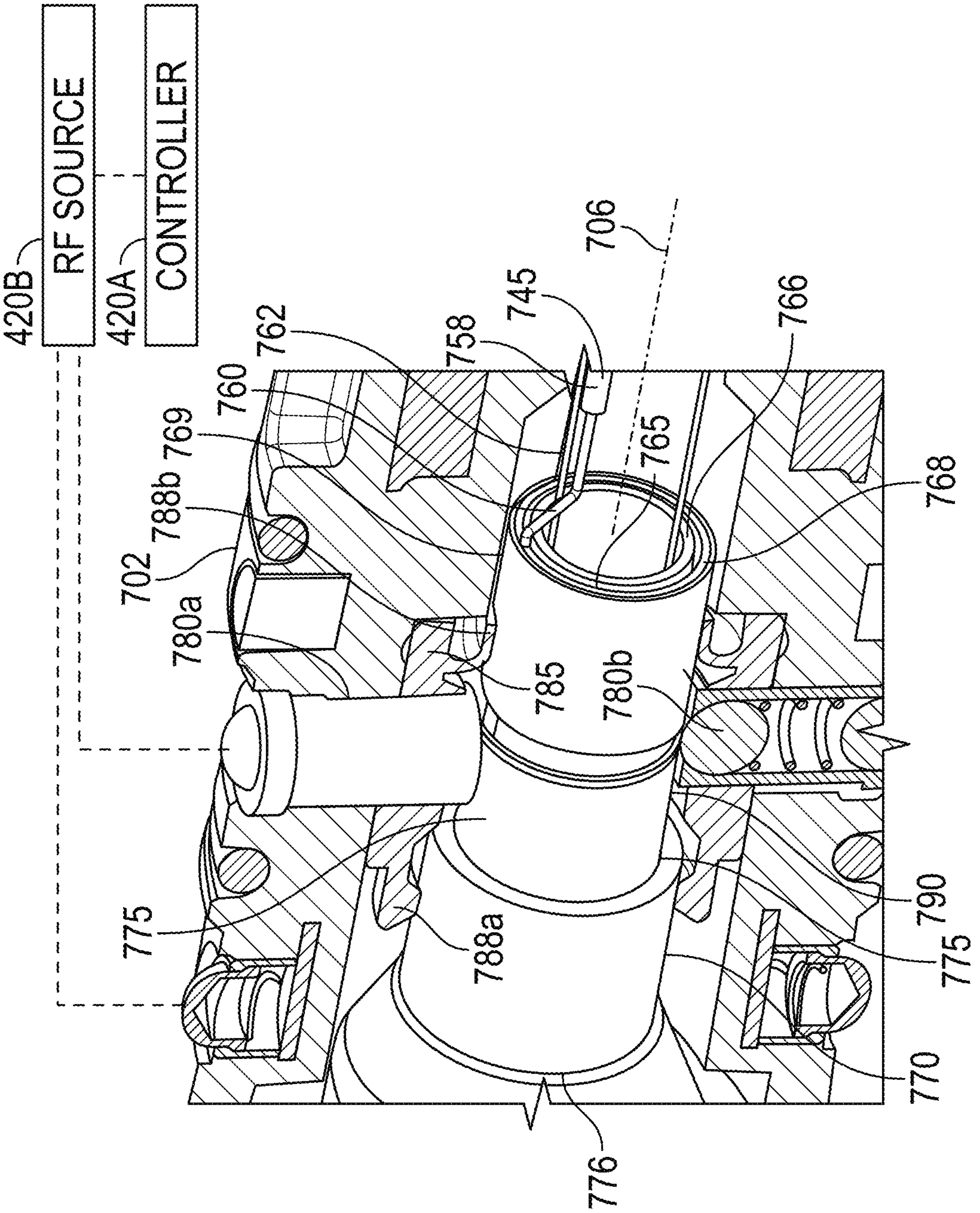
FIG. 26 is an enlarged sectional view of a portion of the hub of the probe of FIG. 25B.

Now turning to FIGS. 25A and 25B, a perspective view and a cut-away view of the hub 702 are shown. FIG. 26 is an enlarged cut-away view of an interior portion of the hub 702. As can be seen in FIGS. 25B and 26, the hypotube 745 carries the electrical lead 718 that extends through the inner tubular member 724. As can be seen in FIG. 25B, the tubular member 724 extends through the hub 702 and the hypotube 745 has a proximal end 758 in the interior of the hub. The proximal end portion 760 of the electrical lead 718 is curved outwardly through a slot 762 in the tubular member 724 and then extends in an interface 765 between two polymer collars 766 and 768 that together provide a seal over and around the insulation layer on the electrical lead 718. Thereafter, a heat shrink material 769 such as FEP can disposed over the collars 766 and 768 (FIG. 26). In FIGS. 25B and 26, it can be seen that a polymeric coupling sleeve 770 is fixed to the proximal end portion 772 of the tubular member that extends proximally to the drive coupler 774 which is adapted for coupling to the motor drive of the handpiece (not shown). FIGS. 25B and 26 further show conductive metal contact ring 775 is disposed over the insulative coupling sleeve 770. As can be seen in FIG. 26, on the proximal side of the contact ring 775, another polymeric collar 776 is shown that again is covered with an FEP or other heat shrink material. Still referring to FIG. 26, the proximal-most end 777 of electrical lead 718 with its insulator layer removed is in contact with and electrically coupled to the rotating contact ring 775. In turn, the contact ring 775 interfaces with spring-loaded ball contacts 780*a* and 780*b* in the handpiece (not shown) to carry RF current to from RF source 720B to the active electrode 735 (FIG. 22) Spring-loaded ball contacts 782*a* and 782*b* in the hub are adapted to carry current to or from the outer sleeve assembly 710 which comprises a return electrode. It should be appreciated that conductive fluid can migrate into various parts of the hub 702 and it is necessary to prevent any migration of conductive fluid into the interface between the spring-loaded ball contacts 780*a* and 780*b* and the rotating contact ring 775. Any migrating conductive fluid is effectively a return electrode and could cause a short circuit. To insure that there is no migration conductive fluid into contact with contact ring 775, FIGS. 25B and 26 illustrate a flexible seal 785 that has is flexible annular sealing elements 788*a* and 788*b* that are both proximal and distal from the rotating contact ring 775. By the means, the chamber 790 in which the spring-loaded ball contacts 780*a* and 780*b* engage the contact ring 775 will remain fluid-tight.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising." "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A tissue resecting probe, comprising:

a proximal hub; and an elongate shaft assembly that extends distally from the proximal hub to a working end of the tissue resecting probe, the elongate shaft assembly including a metal outer sleeve with a proximal end that is fixedly attached to the proximal hub, the metal outer sleeve further including an outer cutting window formed in a first distal side of the metal outer sleeve, the outer cutting window communicating with an axial bore in the metal outer sleeve that extends proximally from the outer cutting window back through the metal outer sleeve, the elongate shaft assembly further including an inner sleeve that is rotatably received in the axial bore in the metal outer sleeve, the inner sleeve including a distal portion with an inner cutting window formed therein, the inner cutting window including a first sharp metal cutting edge extending around at least part of the inner cutting window, the outer cutting window including a second sharp metal cutting edge extending around at least part of the outer cutting window, the inner sleeve rotatable in the axial bore in the metal outer sleeve for moving the first sharp metal cutting edge past the second sharp metal cutting edge for resecting tissue at the working end of the tissue resecting probe, the inner cutting window communicating with an axial extraction channel in the inner sleeve that extends proximally from the inner cutting window back through the inner sleeve for connecting to a negative pressure source;

wherein the distal portion of the inner sleeve includes a generally tubular metal structure that includes a first opening in a first side thereof that provides the inner cutting window and a second opening in a second side thereof in which a dielectric insert is received such that the dielectric insert is circumferentially spaced apart from the inner cutting window around the generally tubular metal structure, the dielectric insert carrying an active electrode such that at least a first part of the active electrode is left exposed along an outer surface of the dielectric insert, wherein the active electrode with such positioning is circumferentially spaced apart from the inner cutting window around the distal portion of the inner sleeve such that the inner cutting window and the active electrode are alternately rotatable into alignment with the outer cutting window as the inner sleeve is rotated in the axial bore in the metal outer sleeve, wherein the outer cutting window in the metal outer sleeve is circumferentially wider than the dielectric insert such that the dielectric insert may be stopped within the outer cutting window to leave a marginal portion of the generally tubular metal structure exposed between the dielectric insert and the second sharp metal cutting edge of the outer cutting window, the marginal portion of the generally tubular metal structure configured to act as a first return electrode in the tissue resecting probe for inhibiting current concentration at the second sharp metal cutting edge, the second sharp metal cutting edge configured to act as a second return electrode in the tissue resecting probe.

2. The tissue resecting probe of claim 1, wherein the generally tubular metal structure and the dielectric insert have mating longitudinal surfaces that extend along an interface between the generally tubular metal structure and the dielectric insert.

3. The tissue resecting probe of claim 2, wherein the dielectric insert is slidably received in an axial channel in the generally tubular metal structure.

4. The tissue resecting probe of claim 1, wherein the generally tubular metal structure provides a metal annular portion and the dielectric insert provides a dielectric annular portion that is circumferentially adjacent the metal annular portion.

5. The tissue resecting probe of claim 4, wherein, in a region of the distal portion of the inner sleeve proximal of the inner cutting window, a combination of the metal annular portion and the dielectric annular portion extend a full 360° about the distal portion of the inner sleeve viewed in a transverse cross-section.

6. The tissue resecting probe of claim 1, wherein the active electrode comprises an active electrode insert slidably received in the dielectric insert.

7. The tissue resecting probe of claim 6, wherein the active electrode insert comprises at least a first leg received in a receiving channel in the dielectric insert, the first leg extending proximally from the first part of the active electrode left exposed along the outer surface of the dielectric insert.

8. The tissue resecting probe of claim 6, wherein an outer surface of the active electrode insert extends over an arc of at least 20° viewed in transverse cross-section.

9. The tissue resecting probe of claim 8, wherein an outer surface of the dielectric insert extends over an arc of at least 10° on each side of the active electrode insert viewed in transverse cross-section.

10. The tissue resecting probe of claim 9, wherein a distance between the dielectric insert and the first sharp metal cutting edge extends over an arc of at least 10° viewed in transverse cross-section.

11. The tissue resecting probe of claim 6, wherein an outer surface of the active electrode insert and adjacent dielectric portions of the dielectric insert extend over a first arc viewed in transverse cross-section and the outer cutting window extending over a second arc viewed in transverse cross-section, and wherein the second arc is greater that the first arc.

12. The tissue resecting probe of claim 11, wherein the active electrode insert has an outer surface extending circumferentially at least 0.030 inches.

13. The tissue resecting probe of claim 12, wherein an edge of the active electrode insert is spaced-apart from a surface of the generally tubular metal structure closest to the edge of the active electrode insert by at least 0.010 inches.

14. The tissue resecting probe of claim 1, wherein a radius of an outer surface of the active electrode is less than a radius of an outer surface of the dielectric insert by 0.020 inches or less.

15. The tissue resecting probe of claim 14, wherein the radius of the outer surface of the dielectric insert is less than a radius of an outer surface of the generally tubular metal structure by 0.020 inches or less.

16. The tissue resecting probe of claim 1, wherein the active electrode has an outer surface that is diametrically opposed to the inner cutting window.

17. The tissue resecting probe of claim 1, wherein the active electrode has an outer surface that is asymmetrically opposed to the inner cutting window.

18. The tissue resecting probe of claim 1, wherein the inner sleeve is received over and engages a proximal portion of the generally tubular metal structure and a proximal portion of the dielectric insert.

19. The tissue resecting probe of claim 1 further comprising an elongate electrical conductor disposed in the axial extraction channel in the inner sleeve and including a distal end attached to the active electrode.

20. A tissue resecting system comprising:

a tissue resecting probe as in claim 1;

a handpiece configured to removably connect to the proximal hub and including a motor drive adapted to rotate the inner sleeve in the axial bore in the outer sleeve; and a controller adapted to selectively drive the motor drive, to stop motor-driven rotation of the inner sleeve, to deliver ablation current to the active electrode, and to deliver cauterizing current to the active electrode.

* * * * *